(12) United States Patent
Murer et al.

(10) Patent No.: US 9,125,729 B2
(45) Date of Patent: Sep. 8, 2015

(54) BUOYANCY-BASED CERVICAL TRACTION SYSTEM

(71) Applicants: Kenneth H. Murer, Chesterfield, MO (US); Neill M. Wright, St. Louis, MO (US)

(72) Inventors: Kenneth H. Murer, Chesterfield, MO (US); Neill M. Wright, St. Louis, MO (US)

(73) Assignee: Aquatic Therapy Innovations, LLC, Chesterfield, MO (US)

( * ) Notice: Subject to any disclaimer, the term of this patent is extended or adjusted under 35 U.S.C. 154(b) by 211 days.

(21) Appl. No.: 13/657,685

(22) Filed: Oct. 22, 2012

(65) Prior Publication Data

US 2013/0211306 A1 Aug. 15, 2013

Related U.S. Application Data

(60) Provisional application No. 61/550,199, filed on Oct. 21, 2011.

(51) Int. Cl.
*A61F 5/00* (2006.01)
*A61H 1/02* (2006.01)
(Continued)

(52) U.S. Cl.
CPC . *A61F 5/012* (2013.01); *A61F 5/04* (2013.01); *A61F 5/042* (2013.01); *A61F 5/048* (2013.01); *A63B 21/1407* (2013.01); *A63B 23/025* (2013.01); *A63B 31/02* (2013.01); *A61F 5/05* (2013.01); *A61F 5/055* (2013.01); *A61F 5/05816* (2013.01); *A61F 5/05883* (2013.01); *A61H 1/0218* (2013.01); *A63B 2225/09* (2013.01); *A63B 2225/605* (2013.01); *B63C 9/08* (2013.01); *B63C 9/13* (2013.01); *B63C 2009/133* (2013.01)

(58) Field of Classification Search
CPC ........... A61F 5/012; A61F 5/04; A61F 5/042; A61F 5/05; A61F 5/055; A61F 5/05816; A61F 5/05588; A61H 1/0218; B63C 9/08; B63C 9/13; B63C 2009/133
USPC ............. 602/13, 18, 32, 36; 441/123; 601/33, 601/39, 148, 151; 606/201
See application file for complete search history.

(56) References Cited

U.S. PATENT DOCUMENTS 100,906 A 3/1870 Krejci
120,089 A 10/1871 Ormsbee
(Continued)

FOREIGN PATENT DOCUMENTS

WO 2007102131 A1 9/2007

OTHER PUBLICATIONS

International Search Report regarding corresponding PCT/US2012/061371, dated Apr. 1, 2013, 3 pages.
(Continued)

*Primary Examiner* — Alireza Nia
*Assistant Examiner* — Keri J Nelson
(74) *Attorney, Agent, or Firm* — Senniger Powers LLP

(57) ABSTRACT

A buoyancy-based cervical traction system has a floatation and a head rest supported by the flotation system. The head rest is adapted to support a person's head above the neck and apply traction to the neck when the person is in a body of liquid. The system has a position adjustment system adapted to allow selective adjustment of the position at which the person's head rest will be relative to an upper surface of the liquid when the person and the cervical traction system are in the liquid, the person's head is supported by the head rest, and the cervical traction system and person are floating in the liquid at equilibrium.

17 Claims, 20 Drawing Sheets

(51) Int. Cl.
  *A61F 5/01*      (2006.01)
  *A61F 5/04*      (2006.01)
  *A61F 5/042*     (2006.01)
  *A63B 23/025*    (2006.01)
  *A61F 5/048*     (2006.01)
  *A63B 21/00*     (2006.01)
  *A63B 31/02*     (2006.01)
  *B63C 9/08*      (2006.01)
  *A61F 5/05*      (2006.01)
  *A61F 5/055*     (2006.01)
  *A61F 5/058*     (2006.01)
  *B63C 9/13*      (2006.01)

(56) References Cited

U.S. PATENT DOCUMENTS

| | | | |
|---|---|---|---|
| 206,397 A | 7/1878 | Marx | |
| 1,043,367 A | 11/1912 | Smack | |
| 1,225,023 A | 5/1917 | Foote | |
| 1,385,581 A | 7/1921 | Pallady | |
| 1,400,976 A | 12/1921 | Parmele | |
| 1,544,672 A | 7/1925 | Milbury | |
| 1,579,502 A | 4/1926 | Blakeslee | |
| 1,806,786 A | 5/1931 | Claus | |
| 2,210,809 A | 8/1940 | Gray | |
| 2,890,467 A | 6/1959 | Cowell | |
| 3,048,860 A | 8/1962 | Richardson | |
| 3,633,230 A | 1/1972 | Horton | |
| 3,750,205 A | 8/1973 | Pfeifer | |
| 4,722,329 A | 2/1988 | Kalvag | |
| 4,798,550 A | 1/1989 | Biancucci | |
| 4,800,871 A | 1/1989 | Florjancic | |
| 4,925,419 A | 5/1990 | Susanna | |
| 5,092,589 A | 3/1992 | Packer | |
| 5,105,804 A | 4/1992 | Van Nostrand | |
| 5,258,018 A | 11/1993 | Van Nostrand | |
| 5,409,412 A | 4/1995 | Colon | |
| 5,776,088 A * | 7/1998 | Sereboff | 602/19 |
| 5,779,512 A | 7/1998 | Rupert | |
| 6,042,602 A | 3/2000 | Wells | |
| 6,659,825 B2 | 12/2003 | Foss | |
| 6,767,267 B2 | 7/2004 | Miller | |
| 6,827,697 B1 | 12/2004 | Liepman | |
| 6,843,694 B2 | 1/2005 | Simmons | |
| 6,887,186 B2 | 5/2005 | Bambanian | |
| 6,948,991 B2 | 9/2005 | Zhao | |
| 7,186,158 B1 | 3/2007 | Barber et al. | |
| 2002/0094735 A1 | 7/2002 | Lariviere | |
| 2003/0236040 A1 | 12/2003 | Miller | |
| 2005/0101204 A1 | 5/2005 | Zhao | |
| 2010/0094342 A1* | 4/2010 | Fischer | 606/241 |

OTHER PUBLICATIONS

Written Opinion of the International Searching Authority, PCT/US2012/061371, dated Apr. 1, 2013, 5 pages.

* cited by examiner

BUOYANCY-BASED CERVICAL TRACTION SYSTEM

CROSS REFERENCE TO RELATED APPLICATION

The present application claims priority to U.S. provisional application No. 61/550,199, filed Oct. 21, 2011, the entire contents of which are hereby incorporated by reference.

FIELD OF INVENTION

The present invention relates generally to systems and method of applying traction to a person's neck and more particularly to systems and methods for using a buoyant apparatus to support a person partially immersed in a liquid in a manner that applies cervical traction to the person.

BACKGROUND

Cervical traction is a mainstay for conservative treatment of many problems in the neck, including, but not limited to, herniated discs in the cervical spine, degenerative disc disease of the cervical spine, osteoarthritis/arthritis of the cervical spine, radicular arm pain, axial neck pain, and whiplash. The goals of traction include, but are not limited to, decompressing a pinched nerve, regenerating the cervical discs, stretching the neck, and providing pain relief. The primary method of cervical traction has been in-line, over-the-door cervical traction.

An example of an over-the-door cervical traction device is illustrated in U.S. Pat. No. 3,695,256. This type of cervical traction, while effective, has several significant limitations:
1. It is quite uncomfortable, with patients complaining of the sensation of being hung.
2. It provides traction only in one direction—with the traction force directed straight upward.
3. It is difficult for one person to successfully place the traction device on without assistance from another person.

The present inventor has developed a buoyancy based cervical traction system that provides advantages over over-the-door and other types of cervical traction systems, as will be described in detail below.

SUMMARY

One aspect of the present invention is a buoyancy-based cervical traction system for applying cervical traction to a person partially submerged in a liquid. The system includes a floatation system having positive buoyancy when in the liquid and a head rest supported by the flotation system. The head rest is adapted to support the person's head above the neck and apply traction to the neck when the person is in the liquid. The system also includes a position adjustment system adapted to allow selective adjustment of a position at which the head rest will be relative to an upper surface of the liquid when the person and the cervical traction system are in the liquid, the person's head is supported by the head rest, and the cervical traction system and person are floating in the liquid at equilibrium.

Another aspect of the invention is a buoyancy-based cervical traction system for applying cervical traction to a person partially submerged in a liquid. The system has a head rest adapted to support the person's head above the neck and a floatation system having positive buoyancy when in the liquid. The head rest is supported by the floatation system so the system exerts an upward force on the person's head when the person and the system are in the liquid and the person's head is supported by the head rest. The system also includes a head rest orientation adjustment system adapted to allow selective adjustment to an orientation at which the head rest will be relative to the flotation system.

Still another aspect of the invention is a method of applying cervical traction to a person partially submerged in a liquid. The method involving supporting the person's head above the neck by a head rest while the head rest is supported by a floatation system in the liquid. The method also includes adjusting at least one of the head rest and floatation system to adjust the position of the head relative to the surface of the liquid when the person and the floatation system are floating in the liquid at equilibrium.

Yet another aspect of the invention is a buoyancy-based cervical traction system for applying cervical traction to a person partially submerged in a liquid. The system includes a floatation system having positive buoyancy when in the liquid. A head rest is supportable by the floatation system so the system exerts an upward force on the person's head when the person and the system are in the liquid and the person's head is supported by the head rest. The head rest includes a chin support for supporting the person's chin. The chin support and floatation system are adapted so the chin support is secured to the floatation system by the weight of the person.

Still another aspect of the invention is a buoyancy-based cervical traction system for applying cervical traction to a person partially submerged in a liquid. The system has a floatation system having positive buoyancy when in the liquid. A head rest is supportable by the floatation system so the system exerts an upward force on the person's head when the person and the system are in the liquid and the person's head is supported by the head rest. The head rest includes a chin support for supporting the person's chin. The chin support is adapted to yield in a manner that results in separation of the chin support from the floatation system in response to any forces in excess of a cervical traction limit.

Other objects and features will in part be apparent and will in part be pointed out hereinafter.

DETAILED DESCRIPTION

Figure 11:
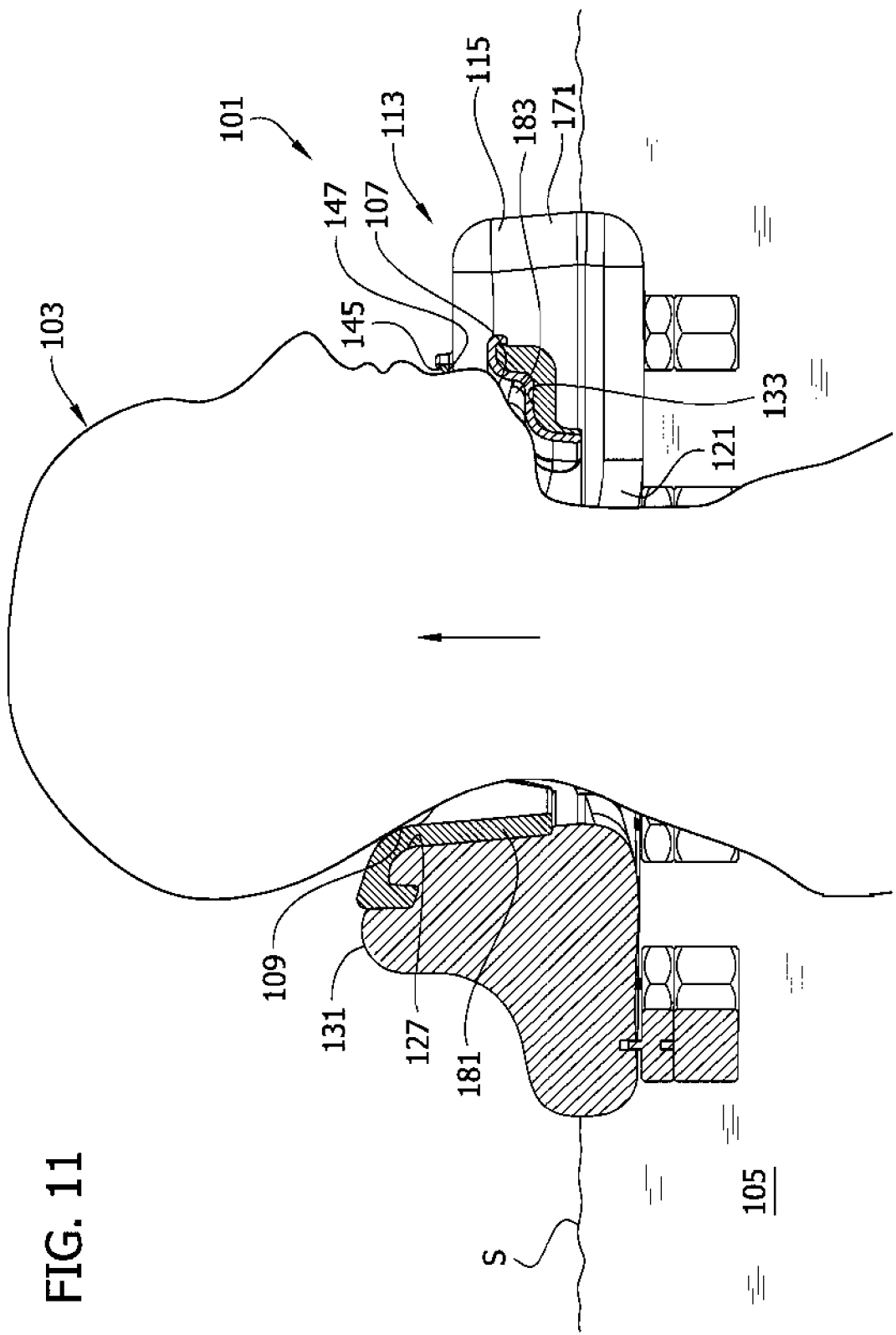
FIG. 11 is a cross section of the cervical traction system taken in a plane including line 11-11 on FIG. 5 showing a person supported by the cervical traction system in a body of liquid.
Figure 12:
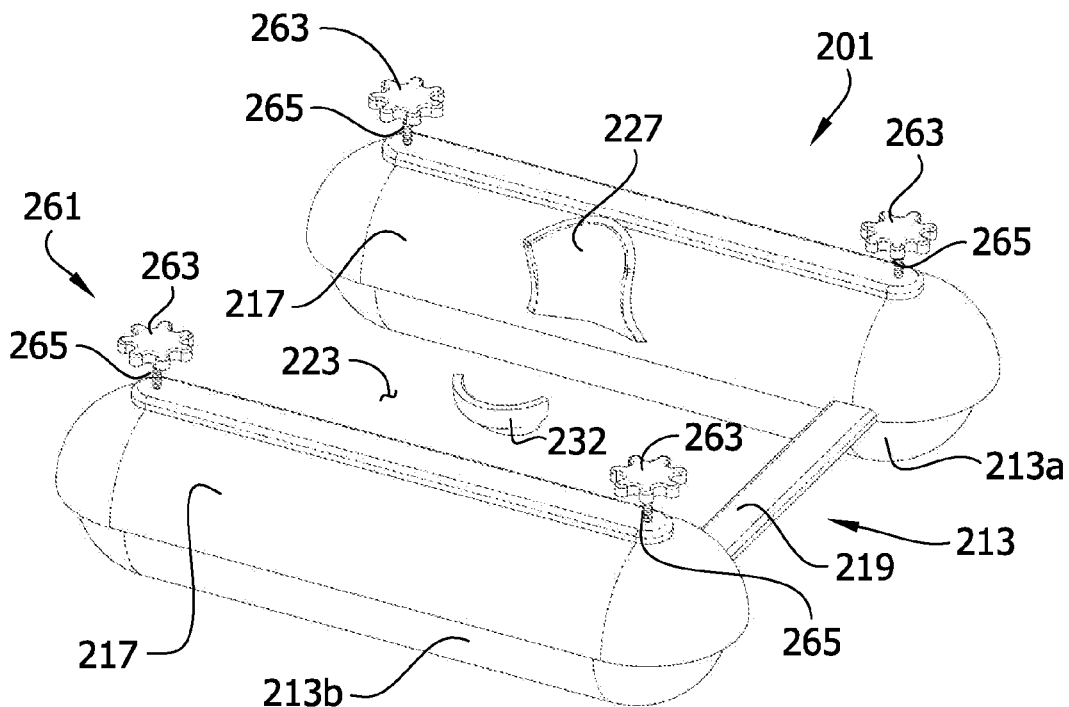
FIG. 12 is a perspective of another embodiment of a cervical traction system.
Figure 13:
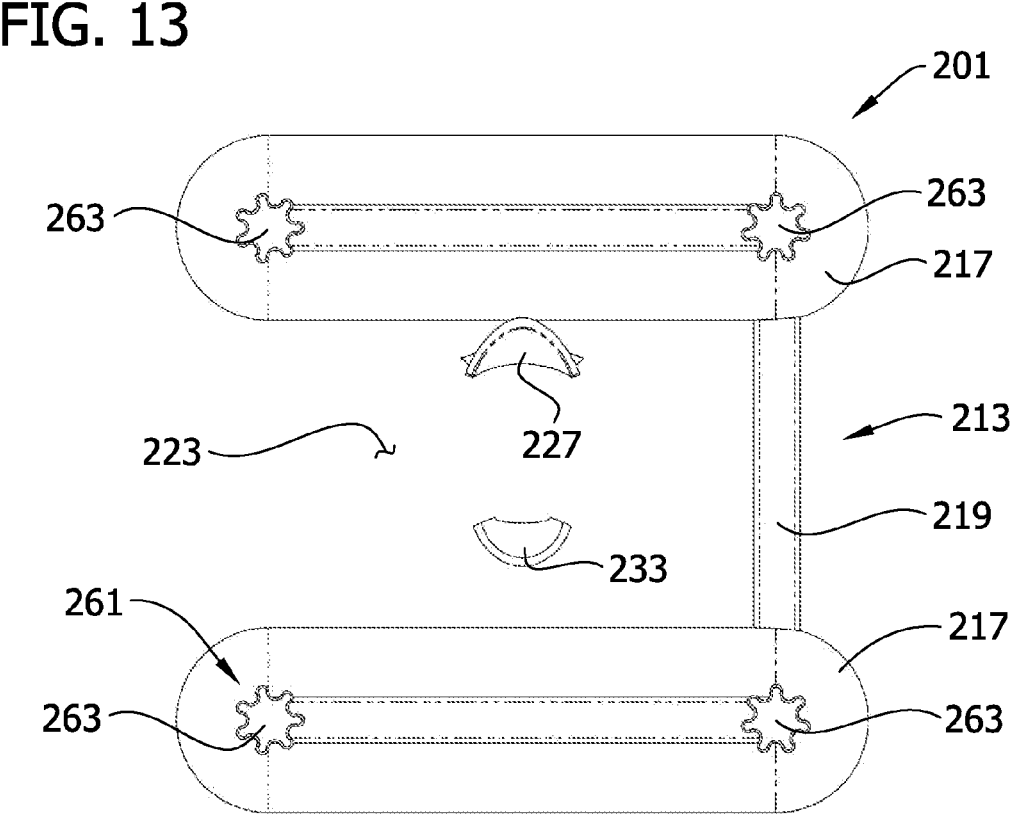
FIG. 13 is a top plan view of the cervical traction system illustrated in FIG. 12.
Figure 14:
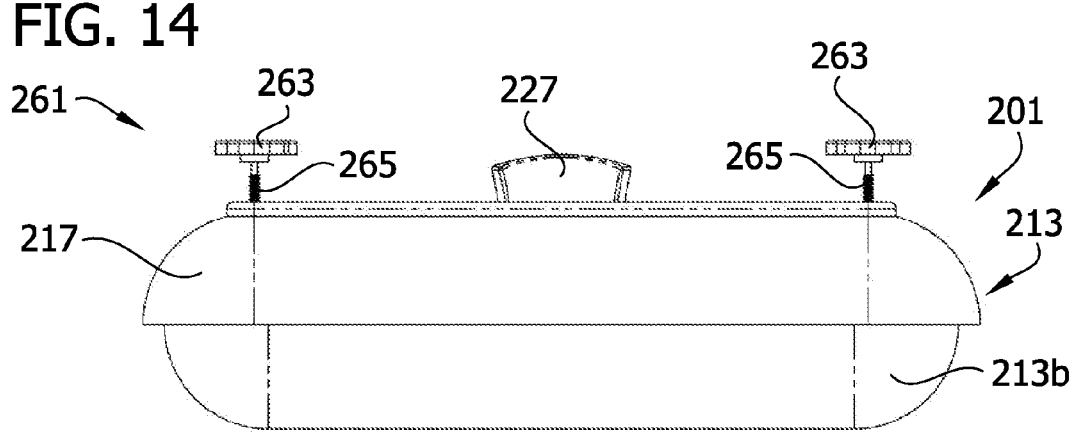
FIG. 14 is a front elevation of the cervical traction system illustrated in FIG. 12.
Figure 15:
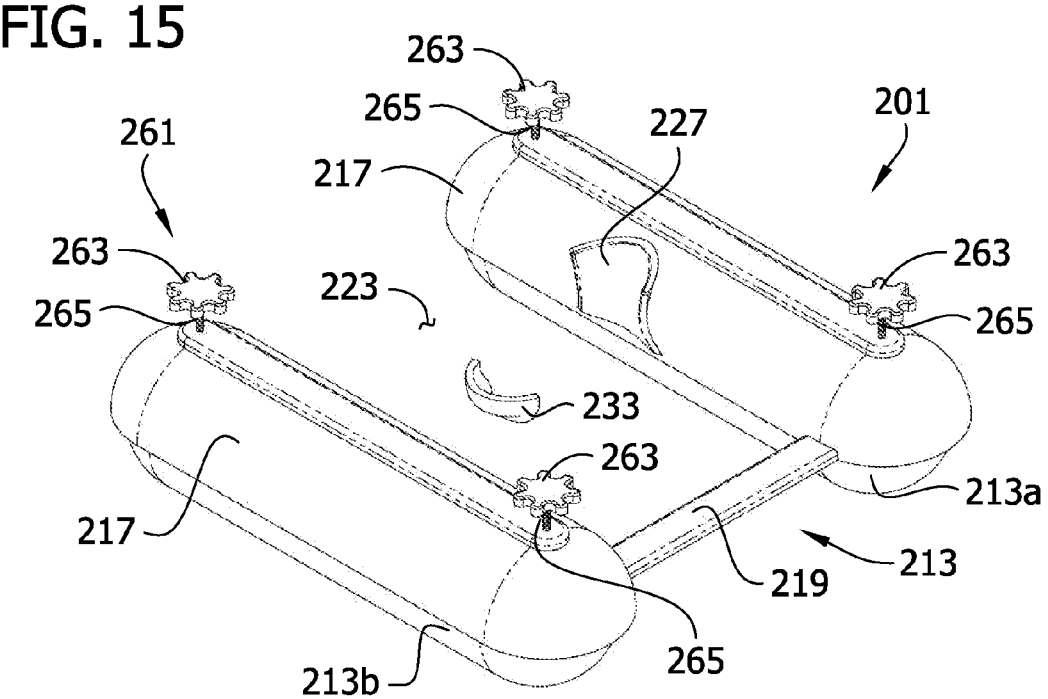
FIG. 15 is another perspective of the cervical traction system illustrated in FIG. 12.
Figure 16:
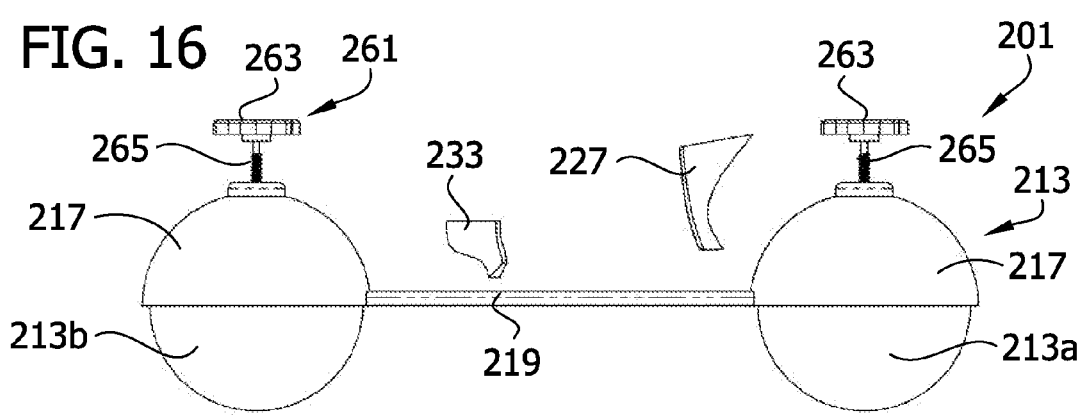
FIG. 16 is a side elevation of the cervical traction system illustrated in FIG. 12.

One embodiment of a buoyancy-based cervical traction system is illustrated in FIGS. 1-11, is generally designated 101. The system 101 is designed to support a person 103 (FIG. 11) in a body of liquid 105 (e.g., a pool or tub of water or other liquid) so the person's head is above the surface S of the liquid when the person's head is supported by the cervical traction system and the person and cervical traction system are floating in the liquid at their combined equilibrium position. The cervical traction system 101 suitably supports the person 103 at an elevation in the liquid 105 that is above the equilibrium position of the person in the liquid without the additional buoyancy provided by the cervical traction system. Accordingly, the cervical traction system 101 applies an upward force to the person's body, as indicated by the arrow in FIG. 11, to hold the person above the equilibrium position of the person in the liquid. As illustrated in FIG. 11, the cervical traction system 101 suitably engages the person 103 above the neck (e.g., at the chin 107 or lower jaw and at the back of the head 109) so the upward force applied to the person results in cervical traction.

As illustrated in FIGS. 1-11, the cervical traction system 101 includes a floatation system 113 having positive buoyancy when in the liquid 105. In the illustrated embodiment, the floatation system 113 includes a U-shaped collar 115 of buoyant material configured to extend most of the way around the person's 103 neck when the person's neck is at the base of a slot-shaped opening 117 forming the inner margin of the U-shaped collar. The floatation system 113 can be made of any buoyant material. For example, the floatation system 113 can suitably include a blow-molded polymeric rigid shell having the shape of the collar 115 that is filled with air, foam, or other buoyant material. The rigid shell can be covered with a uniform outer layer of foam padding if desired. Also, if desired, a foam pad 181 can be secured to the base of the collar 115 to support the back 109 of the person's 103 head.

As illustrated in FIGS. 2, 4, 5, 7-9, and 11 the lower side of the floatation system 113 is suitably generally flat except for recesses/indentations 121 formed in the lower surface of the floatation system on opposite sides of the U-shaped collar 115 at the base of the slot 117. The recesses/indentations 121 are suitably configured to receive and generally conform to the shoulders of a person 103 wearing the collar 115 around his or her neck.

A head rest 125 is supported by the flotation system 113 and adapted to support the back of the person's head 109 above the neck and apply traction to the neck when the person is in the liquid. As illustrated in FIGS. 1-11, one part 127 of the head rest 125 is a component of the collar 115 configured to support the back of the person's head 109 and another part of the head rest is a chin support 129 that is formed separately from the collar 115 and supported by the floatation system 113 so it is moveable relative to the collar of the floatation system. However, the entire head rest can be formed separately from the collar and the rest of the floatation system within the scope of the invention.

In the illustrated embodiment, the head rest 125, and in particular the rear portion 127 of the headrest, is configured to engage the occiput 109 (i.e., base of the skull at the back of the neck) of the person using the system 101. For example, the rear portion 127 of the head rest 125 in the illustrated embodiment includes the upper surface of a ridge 131 extending around the base of the U-shaped collar 115 at its inner margin. In this embodiment, the highest point on the cervical traction device 101 is at the ridge 131 at the base of the U-shaped collar 115 where the rear portion 127 of the head rest 125 is adapted to engage the occiput 109.

The chin support 129 suitably includes a chin rest 133 shaped to support the person's 103 chin and/or lower jaw. As illustrated in FIGS. 1-11, the chin support 129 has arms 135 extending from opposite sides of the chin rest 133 for connecting the chin rest to the collar 115 of the floatation system 113. In the illustrated embodiment, for example, a pair of support arms 135 extends from each side of the chin rest 133. As illustrated, the floatation system 113 has a pair of tracks 141 extending along the opposite sides of the U-shaped collar 115 on opposite sides of the U-shaped slot 117. For example, in the illustrated embodiment, each track 141 includes a series of ridges or teeth 145 in the upper surface of a plate 147 mounted on top of the collar 115 along a respective side of the collar.

The chin support 129 in this embodiment is mounted on the collar 115 of the flotation system 113 by placing the arms 135 on the plates 147 between corresponding ones of the ridges 145 therein so the chin support can slide toward and away from the bottom of the U-shaped slot 117 along the tracks 141 and over the ridges when the chin support bears little or no weight. Conversely, when the chin support 129 bears the weight of a person 103 using the device 101 its arms 135 are seated in the receptacles formed between the respective ridges 135 so the chin support and chin rest 133 thereof do not move during normal use of the device 101 to apply traction. But even after being secured to the collar 115 in this manner, the chin support 129 can easily separate from the rest of the device 101 to release the person 103 if the device is upturned or other unexpected circumstances arise that would make it undesirable for the person to be held captive within the device.

The ability of the chin support 129 to separate readily from the collar 115 of the floatation system 113 also makes it impractical for a person standing alongside a pool or other body of liquid to arrange the chin support 129 and collar 115 around their neck in a manner that results in the chin support being secured to the collar. This discourages attempts to wear the device 101 while not in the pool or other liquid 105, which could pose a risk of injury particular if a person fell into the pool while wearing the device 101. Moreover, the chin support is suitably adapted to yield in a manner that results in separation of the chin support 129 from the floatation system 113 in response to any forces in excess of a cervical traction limit. For example, the arms 135 of the chin support 129 in the illustrated embodiment are suitably designed to bend in response to excessive force so that the chin support separates and is released by the floatation system 113 in any circumstance that would result in an excessive traction force.

Accordingly, the ridges/teeth 145 constitute a retaining system 151 that is adapted to secure the chin support 129 to the collar 115 of the floatation system while the system 101 is being used in a pool or other liquid. The retaining system 151 also allows selective adjustment to the position of the chin rest 133 to adjust the chin rest to provide a proper fit people having a wide range of neck sizes. The chin rest 133 is suitably positioned lower than the upper support surface of the back part 127 of the head rest 125. This helps hold the person's 103 head in a comfortable forward facing direction, as illustrated in FIG. 11.

The cervical traction device 101 suitably includes a position adjustment system 161 adapted to allow selective adjustment to a position at which the head rest 125, and therefore the person's 103 head, will be relative to the upper surface S of the liquid 105 when the person and the cervical traction system are in the liquid, the person's head is supported by the head rest, and the cervical traction system and person are floating in the liquid at equilibrium. In addition to increasing or decreasing the amount of traction applied to the person 103, the position adjustment system 161 of the illustrated embodiment is adapted to allow the orientation of the head rest 125 relative to the upper surface S of the liquid 105 to be adjusted. This allows the traction force to be applied by the device 101 in a direction that is skewed relative to the normal vertical axis of the person's 103 body if desired. For example, the traction can be applied in a manner that tends to pull the person's 103 head and upper neck to the left or right and/or to the front or back. This can be advantageous for therapeutic reasons.

The ability to adjust the direction of the traction can be helpful in alleviating a compressed nerve in a particular part of the person's 103 body. Patients with axial neck pain from a degenerative disc can benefit from in-line, axial traction. However, patients with a herniated disc causing arm pain often have unilateral symptoms (i.e., right arm only). In these cases, it may be desirable to apply increased traction on the side that has the pain (e.g., tilting the head to the left for a patient having right arm pain). While the main force of traction can still be in the axial direction, increasing the traction on the side having pain can preferentially decompress the affected nerve. Such differential traction can important for patients with herniated discs, foraminal stenosis, osteoarthritis, radiculopathy, radiculitis, and other afflictions.

There are various ways to include a position adjustment feature in the cervical traction device. In the embodiment illustrated in FIGS. 1-11, the cervical traction device 101 includes a set of buoyancy adjusting devices 163. The floatation system 113 is adapted to facilitate selectively adding and/or removing the buoyancy adjusting devices 163 from the floatation system to adjust the position at which the person's 103 head is supported relative to the upper surface S of the liquid 105. This provides an easy way to adjust the amount of traction force applied to the person 103. For example, adding buoyancy to the floatation system 113 by removing weights and/or adding floats will cause the cervical traction system 101 to hold the person 103 farther above his or her equilibrium position and increase the amount of traction force applied. Conversely, decreasing buoyancy by removing floats and/or adding weights will cause the cervical traction system to hold the person closer to his or her equilibrium position and decrease the amount of traction force applied.

The system 101 illustrated in the FIGS. 1-11 includes a set of weights 163 that can be selectively attached and removed from the floatation system 113. As illustrated the weights 163 can be secured to the collar 115 of the floatation system 113 to adjust the buoyancy of the cervical traction device 101. Various systems can be used to attach and release the weights 163 from the cervical traction device. For example, the weights 163 can be secured to the end of a bolt or threaded shaft and the floatation system 115 can include threaded socket inserts 165 into which the bolts can be screwed to releasably secure a weight to the floatation system. Although embodiment illustrated in FIGS. 1-11 uses bolts and threaded socket inserts to secure the weights 163 to the cervical traction device 101, it is understood other types of releasable connectors could be used to secure the weights to the cervical traction device within the scope of the invention. Also, although the buoyancy adjusters 163 depicted in FIGS. 1-11 are all weights some or all of the buoyancy adjusters could be floats instead. Any floats can be attached to the floatation system 113 in the same manner as the weights 163 and can have the same or similar appearance to the weights.

Moreover, the cervical traction device 101 can suitably include a set of buoyancy adjusters 163 that includes weights having multiple different weights and/or floats that have multiple different amounts of positive buoyancy to provide a greater range of options for adjusting the position of the person's head relative to the upper surface of the liquid. For example, the weights 163 in the illustrated embodiment include a relatively smaller weight 163a (e.g., about 1 pound) and a relatively larger weight 163b (e.g., about two pounds). The weights 163a, 163b can be selectively and releasably secured to one another (e.g., using threaded shafts and threaded inserts formed or otherwise provided on the weights to combine two or more weights to form a larger (e.g., 3 pounds or more) that can be secured to a single threaded insert on the floatation system 115. For example, each weight 163a, 163b can include a threaded socket on one end and a threaded shaft on the opposite end.

To increase or decrease the amount of traction without changing the orientation of the traction force, the buoyancy adjusters 163, such as floats or weights, are added in a manner so the moment resulting from adding or removing a first buoyancy adjuster is cancelled or at least approximately cancelled by the addition or removal of one or more other buoyancy adjusters. For example, if a weight 163 is added to one side of the collar 115, an equally heavy weight could be added to the opposite side of the collar to decrease the amount of traction without altering the orientation of the traction force.

Figure 1:
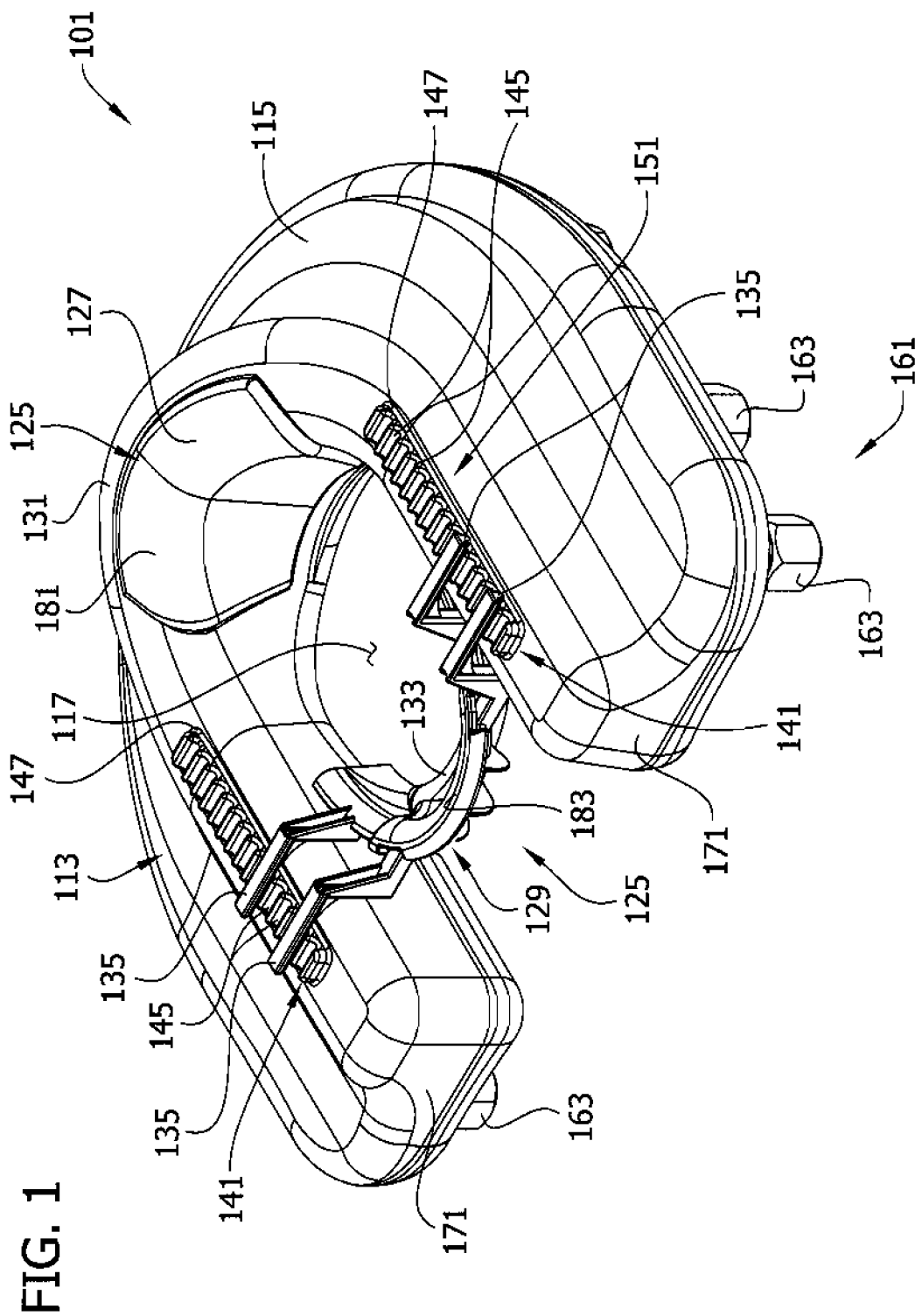
FIG. 1 is a perspective of one embodiment of a buoyancy-based cervical traction system.
Figure 2:
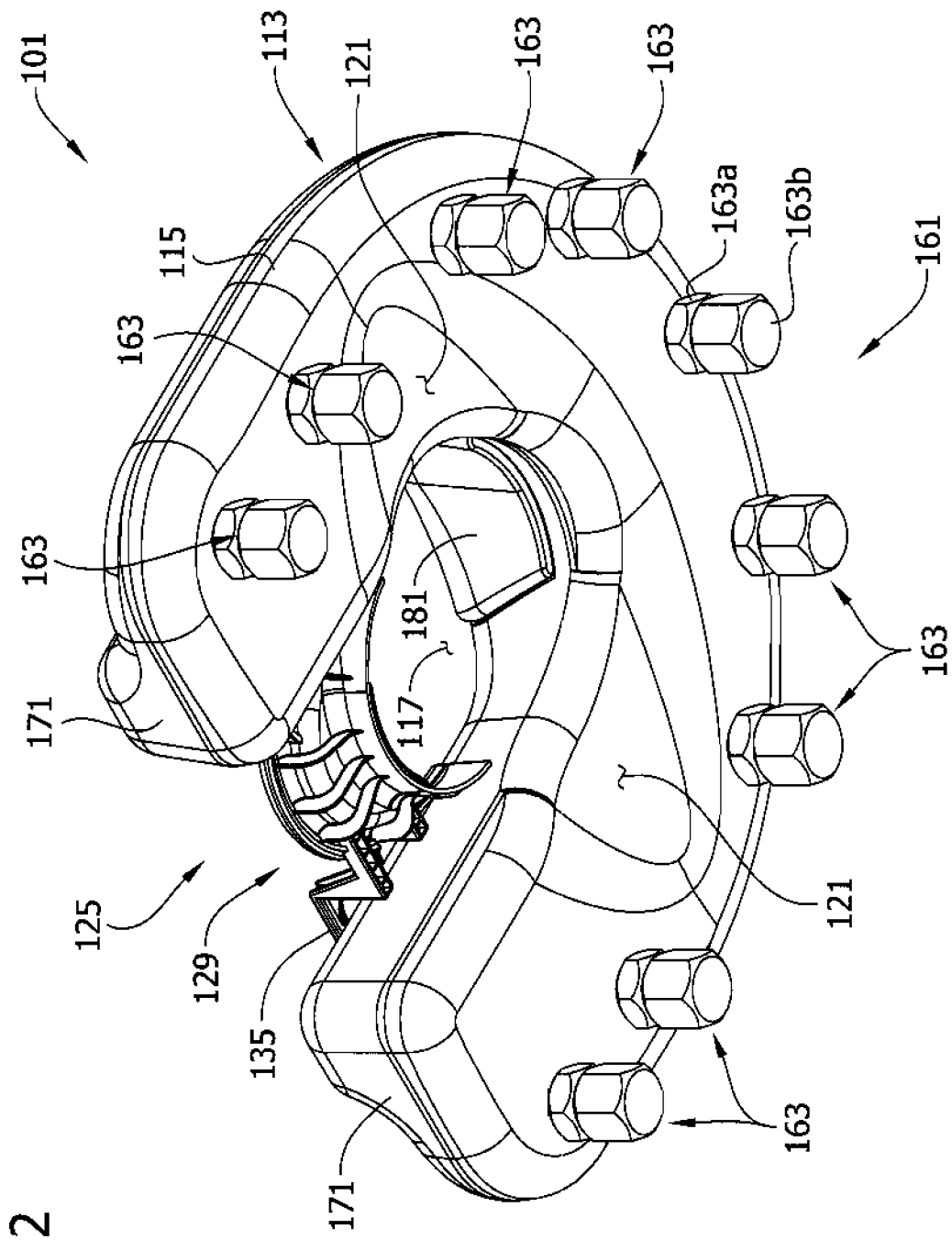
FIG. 2 is another perspective of the buoyancy-based cervical traction system illustrated in FIG. 1 taken from a different vantage point.
Figure 3:
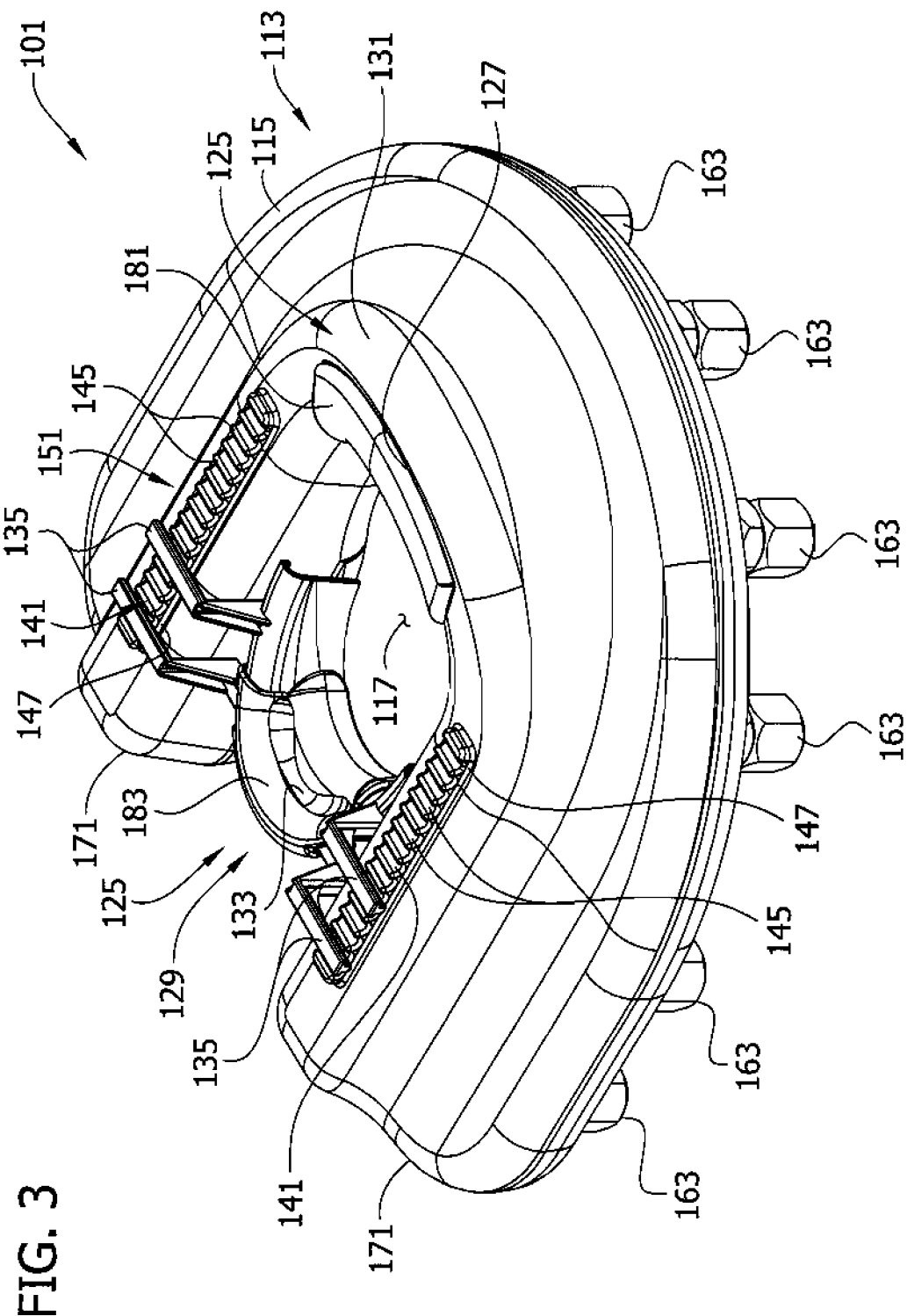
FIG. 3 is another perspective of the buoyancy-based cervical traction system illustrated in FIG. 1 taken from a third vantage point.
Figure 4:
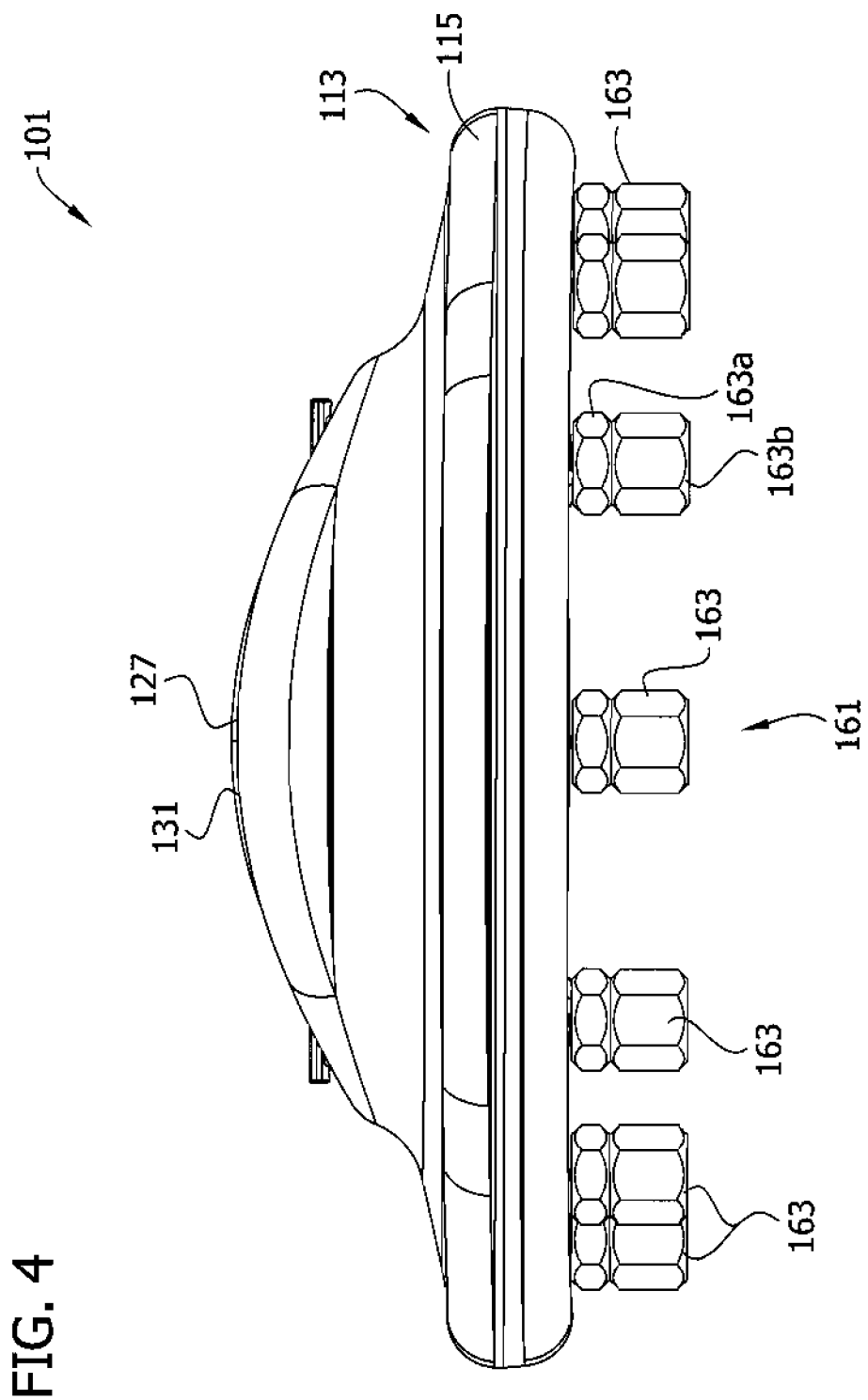
FIG. 4 is a rear elevation of the cervical traction system.
Figure 5:
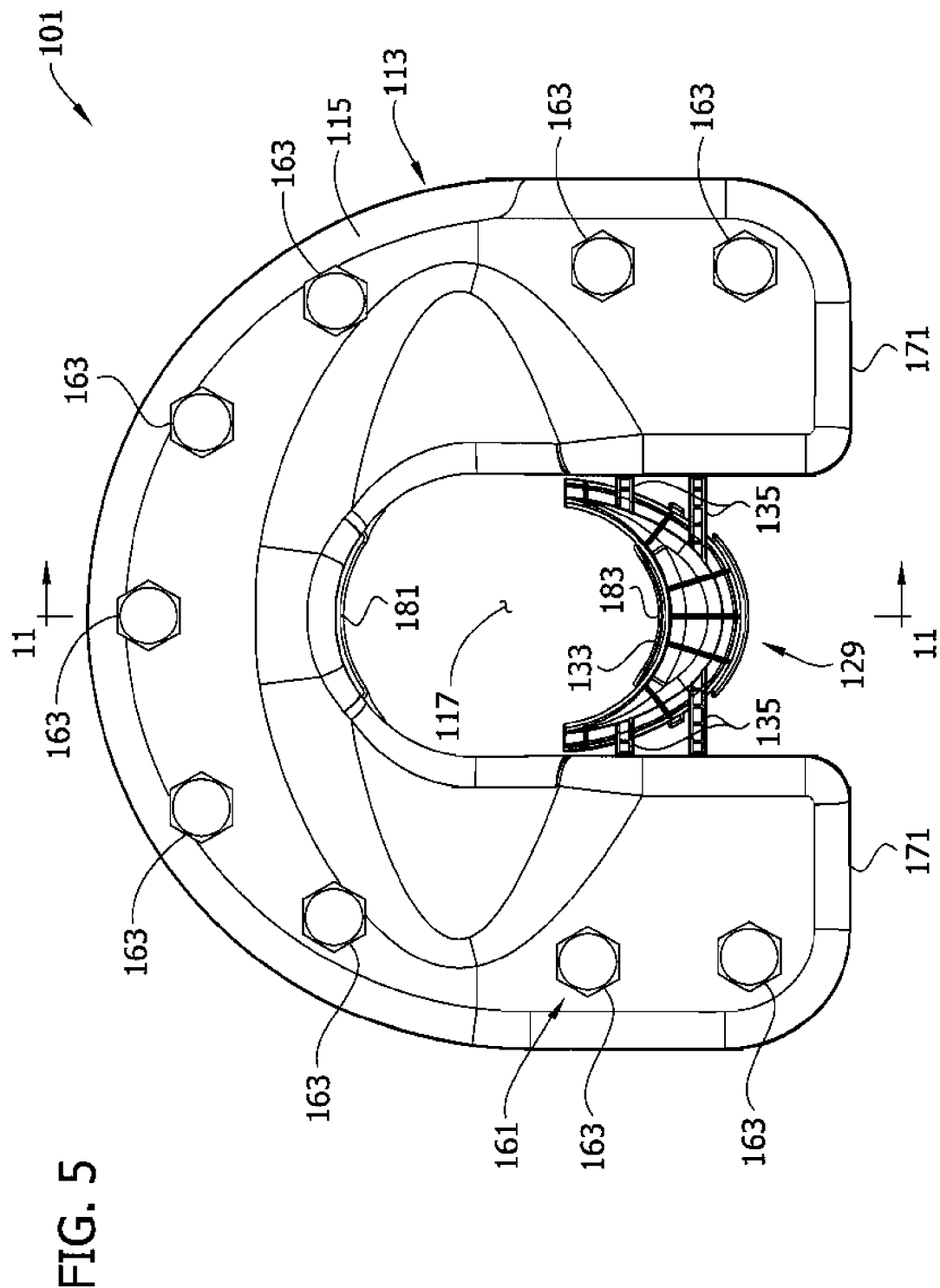
FIG. 5 is a bottom plan view of the cervical traction system.
Figure 6:
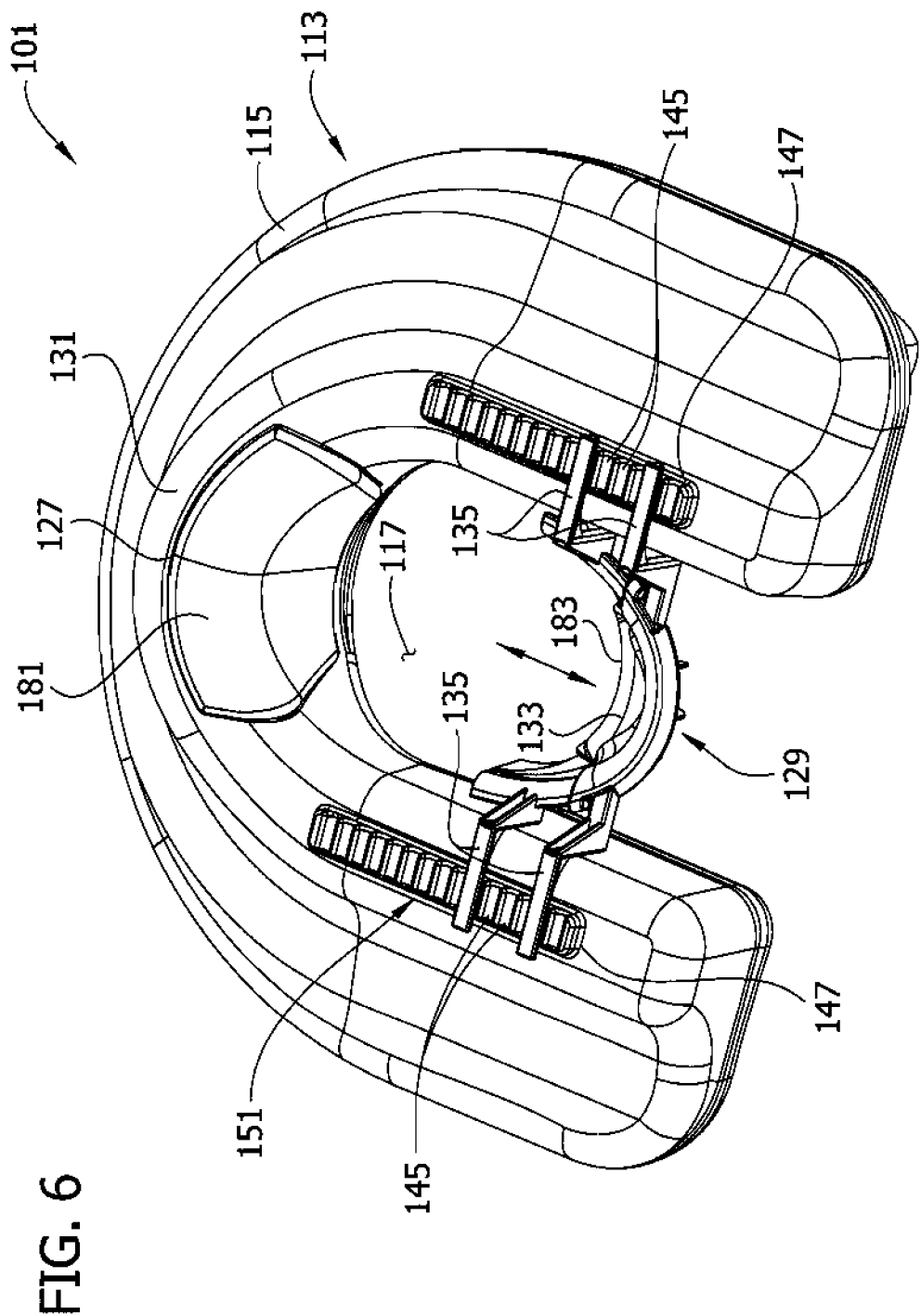
FIG. 6 is another perspective of the cervical traction system illustrating adjustment of a chin rest.
Figure 7:
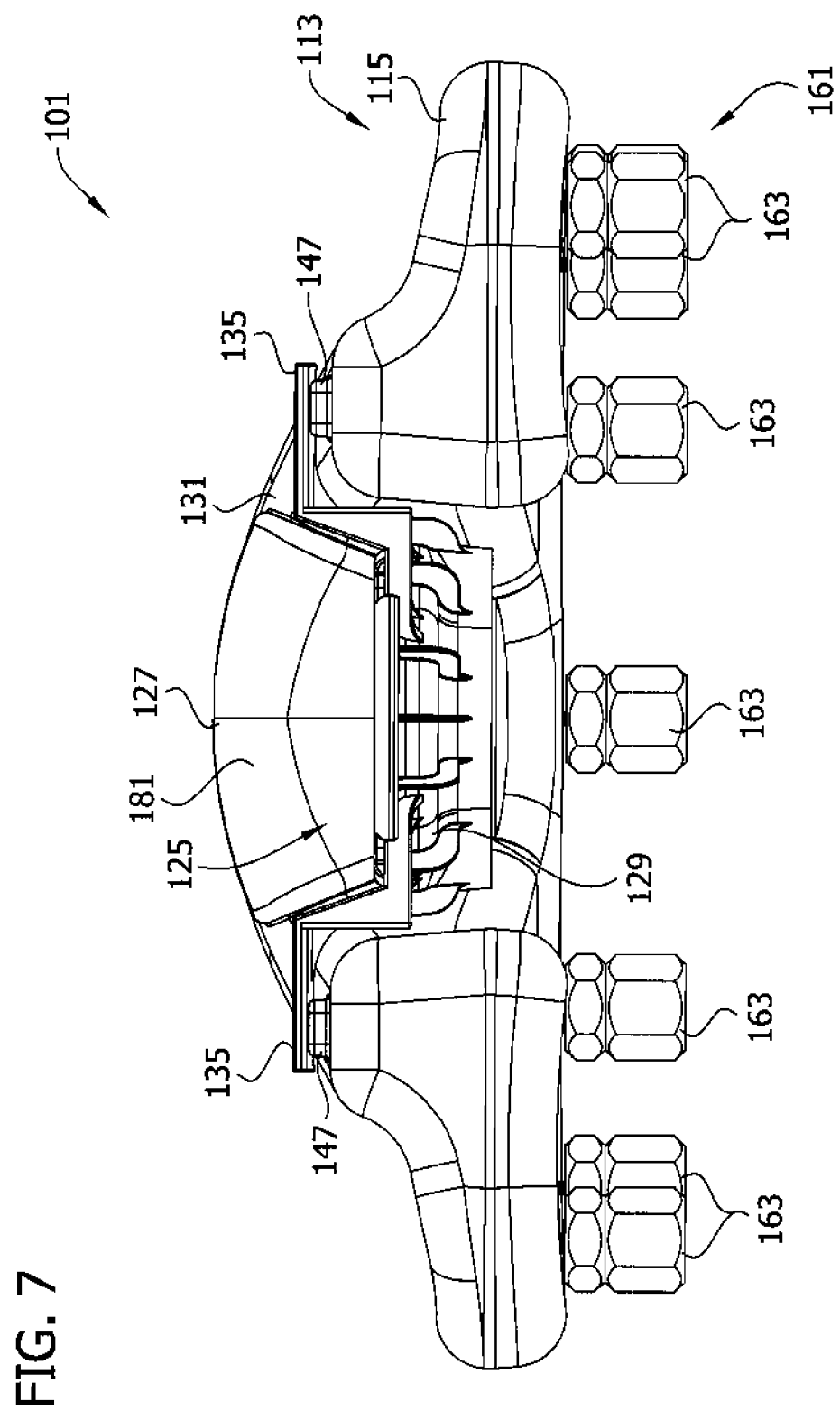
FIG. 7 is a front elevation of the cervical traction system.
Figure 8:
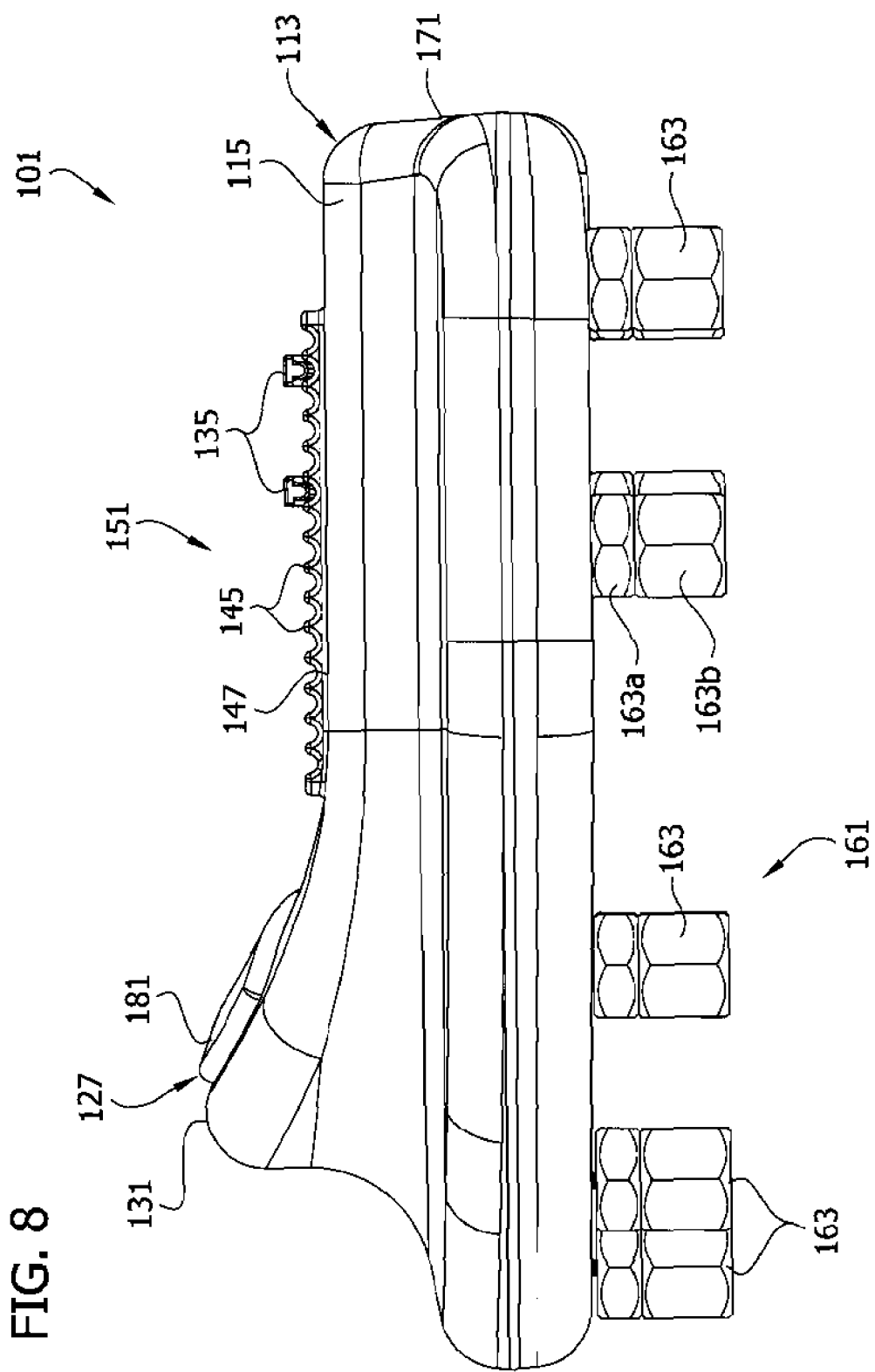
FIG. 8 is a left side elevation of the cervical traction system.
Figure 9:
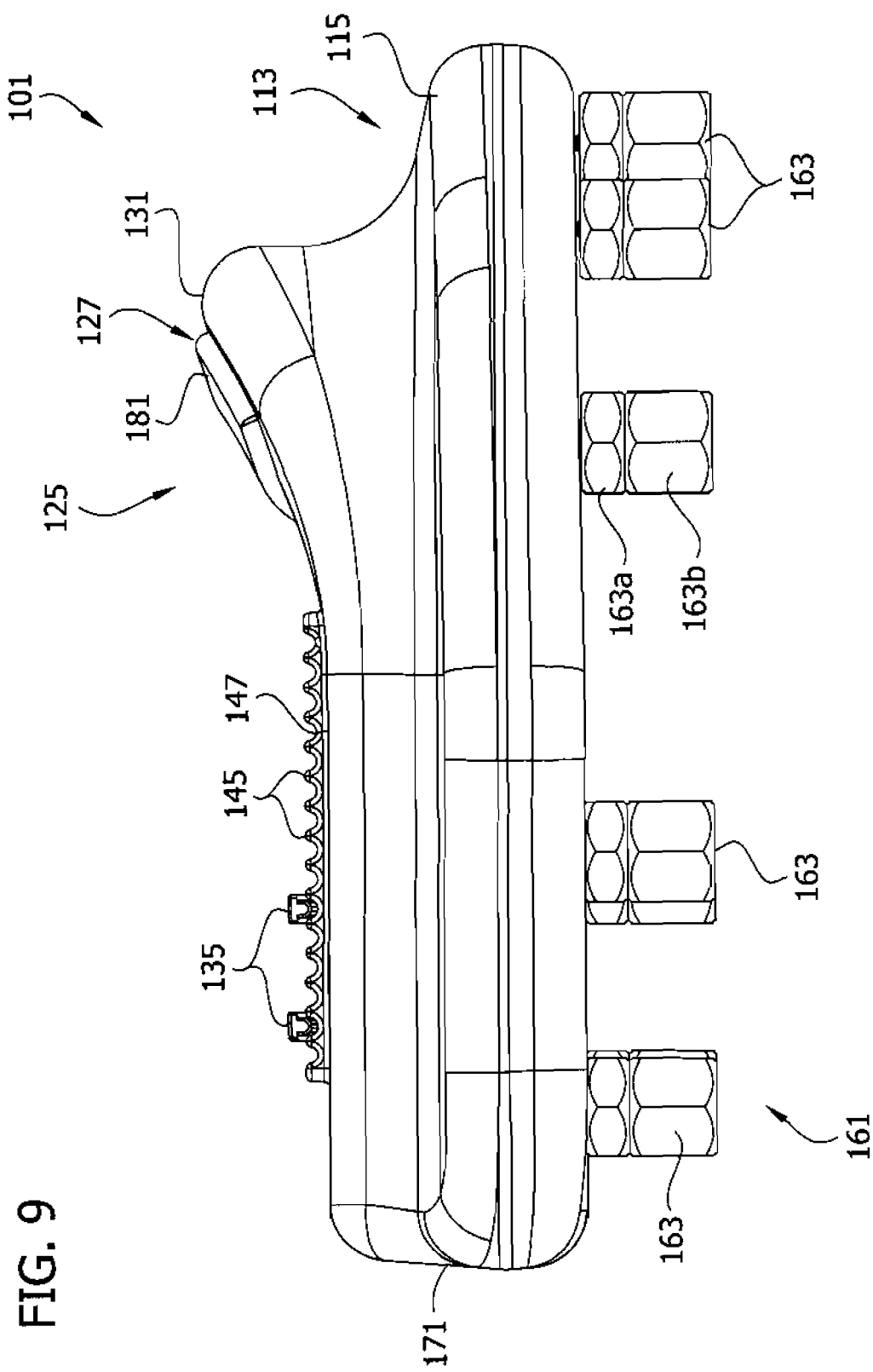
FIG. 9 is a right side elevation of the cervical traction system.
Figure 10:
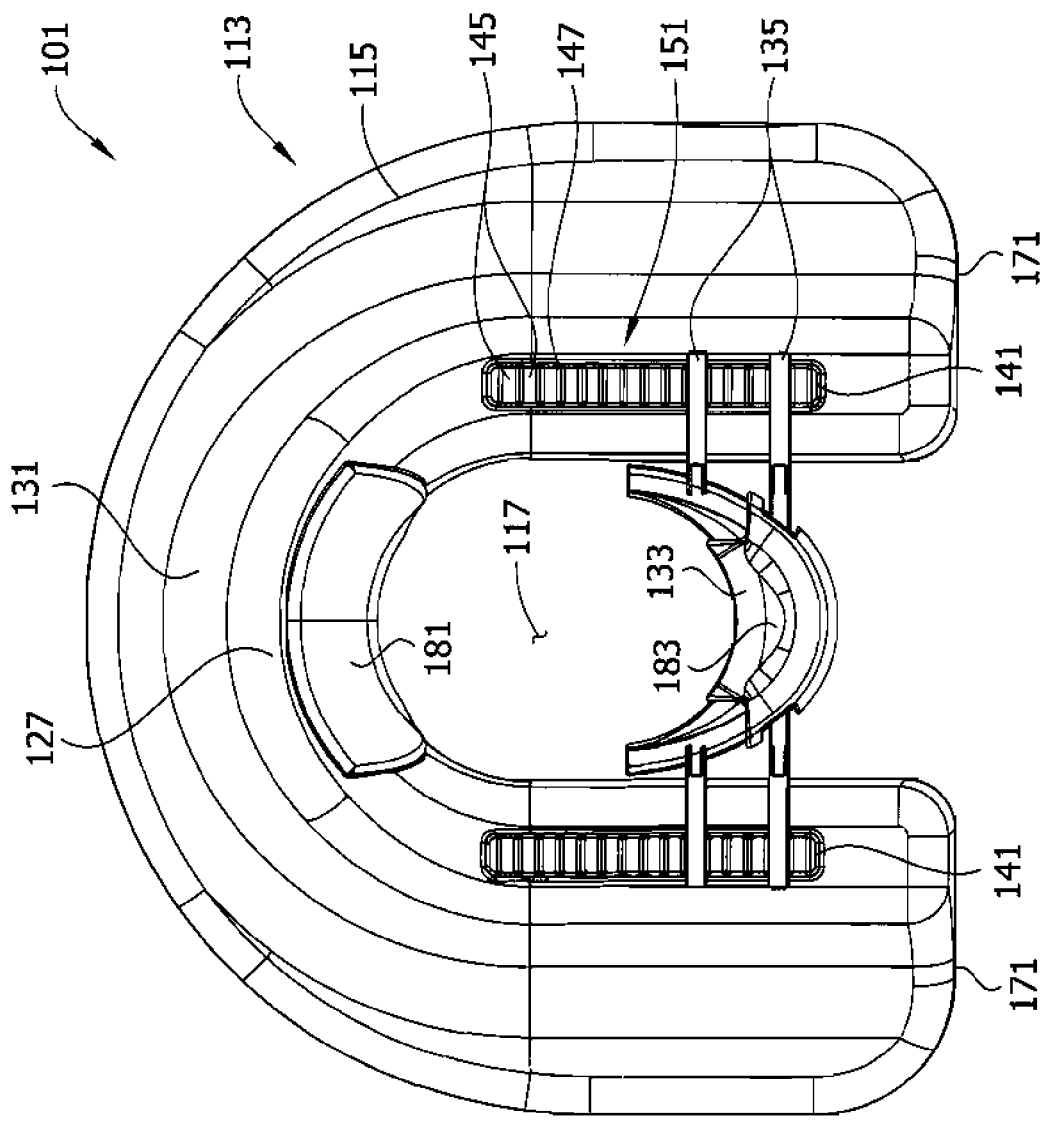
FIG. 10 is a top plan view of the cervical traction system.

On the other hand, the direction of the traction force can be adjusted by adding or removing buoyancy adjusters 163 in an asymmetric manner to the floatation system 113 so the moment resulting from addition or removal of one of the buoyancy adjusters is not completely offset by addition and/or removal of other buoyancy adjusters. As illustrated in FIG. 5, the connectors for attaching the buoyancy adjusters 163 to the floatation system (the position of which corresponds to the position of the weights) are mounted on the underside of the floatation collar 115 of the cervical traction device 101. The connectors and weights 163 secured thereto are suitably positioned closer to the outer margin of the collar 115 than the inner margin of the collar. This increases the length of the lever arm between a buoyancy adjuster 163 that is connected to the collar 115 and the center of gravity of the collar, which facilitates implementing a larger adjustment to the orientation of the traction system using a smaller weight 163 or float.

The connectors are also secured to the collar 115 at multiple different radial positions. This includes multiple different positions that are in front of the person 103 and multiple different positions that are behind the person. This also includes multiple different positions on the left side of the person 103 and multiple different positions on the right side of the person. As illustrated in FIG. 5, the connectors for connecting the weights/floats 163 to the floatation system are arranged in a U-shaped pattern that extends most of the way around the person's 103 neck. Two of the connectors are positioned relatively close to one another at each end 171 of the U-shaped collar 115, as indicated by the weights 163 attached in the corresponding positions in FIG. 5, to account for the inability to locate any connectors at the upper end of the slot 117 in the U-shaped collar. The remaining connectors are suitably spaced generally evenly about the perimeter of the collar, as indicated by the corresponding positions of the weights 163 in FIG. 5. The ability to connect weights 163 and/or floats independently to the floatation system 113 at multiple different radial locations provides the ability to make adjustments to both the pitch and yaw of the floatation system. This provides substantial flexibility to the ability to adjust the direction at which traction is applied to the person using the device.

To use the cervical traction system 101, the collar 115 of the floatation system is placed around the person's neck, so the occiput 109 (back of the head) is resting against the ridge formed on the back of the collar. This is preferably done while the person is already in the pool or other body of liquid. The position of the chin support 129 is adjusted until the chin rest 133 is under the person's chin 107 at the same time the back of the person's head is supported by the ridge 131 on the back of the collar 115 of the floatation system 113. Once the chin support 129 is in position, the weight of the person 103 is allowed to come down on the chin support 129 and seat the arms 135 between corresponding pairs of ridges 145 so the chin support is held securely in position relative to the collar 115 as long as the person 103 remains sufficiently still to maintain somewhat steady pressure on the chin support 129. On the other hand, if the person 103 becomes agitated and thrashes about or is upended for any reason the chin support 129 can easily separate from the collar 115 and thereby allow the person to get out of the device 101 without much difficulty.

If desired, the fit and comfort of the device 101 can be enhanced by using soft inserts 181, 183 for the chin 107 and occiput 109 that can be attached in a variety of ways, such as mild adhesive, Velcro, snaps, etc. These inserts 181, 183 can be applied to both the chin rest 133 and the back 127 of the head rest 125 (e.g., at the inner margin of the collar 115 between the person 103 and the collar). These inserts 181, 183 are suitably single-use, and disposable to provide optimal sanitation. To further account for variations in neck anatomy, the inserts 181, 183 can be used to raise the neck and/or occiput relative the device if necessary. There is considerable variation from one person to the next in the shape and relative position of the base of the head (occiput) and jaw due to variations in skull and jaw shape and due to varying degrees of body mass/obesity. It is important to be able to hold the head in a neutral position notwithstanding the anatomical variations that may be encountered. While the base device is designed to keep an average head in the neutral position, the inserts 181, 183 for either the occipital head rest 127 or chin rest 133 allow individual adjustment to keep the head at a neutral position in the device. The device 101 can easily be placed on a person 103 by themselves without assistance. It is similarly very easy for a person to remove the device without any assistance by lifting the chin support 129 up and sliding it away from their neck.

Once the device 101 is positioned on the person's 103 neck, he or she sits down gently in the water or other liquid 105, or walks slowly down a ramp into a pool containing the liquid. The device 101 is very comfortable compared to over-the-door and similar prior art traction devices. The device 101 is well tolerated due to the natural soothing effects of water and the ability of the person 103 using the device to control their position. The device 101 does not require the person to remain stationary. For example, a person 103 using the cervical traction device 101 in a swimming pool 105 can use their arms and legs to paddle around the pool and change the direction they are facing if they desire. Additionally, because the majority of the person's 103 body is supported by the buoyancy of the liquid 105, the cervical traction device 105 does not tend to cause the person receiving the traction treatment to have the sensation that he or she is being hung. The amount of traction force can be easily changed by adding weights 163 or removing floats to decrease the traction or adding floats or removing weights to increase the traction.

Further, during use weights 163 and/or floats can be added asymmetrically to just one side of the device, or to the front or back of the device to apply differential traction and thereby change the direction of the traction force relative to the person's body. Differential traction can be used to place the neck into more or less extension or flexion. Likewise differential traction can be used to laterally bend the neck to provide further traction to a side of the body experiencing nerve root compression or other ailment. Various combinations of weights and floats can be used together to direct the differential traction in any of a wide range of possibilities. Moreover, weights (not shown) could be added to the person's 103 arms, torso, waist, or legs during use of the device to provide additional traction force or for lower spine manipulation. The person 103 using the device can alleviate the traction force by standing up or walking out the water. As soon as the weight is removed from the chin support 129 during exit of the liquid 105, the chin support 129 will easily and automatically separate from the collar 115 to release the person 103 from the device 101.

The cervical traction system 101 can be used to support other therapeutic treatments as well. For patients 103 with burns, decubitus ulcers or other wounds, for example, treatment may involve taking pressure off of the affected area (where possible) and/or soaking the area in various solutions. Often this is difficult to do, especially in dependent areas like the buttocks (a common area for decubitus ulcers). The cervical traction device can be used to support a patient's 103 weight to allow the affected area to float. The patient could be placed in a large tub of salt solution, mineral waters, or medicated waters in addition to water, depending on the therapeutic need. The option to use the cervical traction device 101 to treat burns, ulcers or other wounds can be a particularly good solution when the patient 103 is obese, elderly, and/or infirm.

The cervical traction system 101 can also be used for recreational purposes. For example, the cervical traction device 101 could be used by an individual 103 for rest or relaxation in a swimming pool, lake, or other body of water. Likewise, the cervical traction system 101 can be used as part of a sensory deprivation or other relaxation treatment (e.g., at a spa or at a resort). In some cases, such as when the system 101 is used primarily for relaxation or sensory deprivation treatments, weights 163 can be added to the floatation system to reduce the traction force to a very light traction force.

The cervical traction system 101 can be equipped with various accessories to improve the experience of the person using it. For example, the device 101 could be equipped with any combination of the following:

MP3 player holder;
Built in speakers for MP3 player;
Built in radio and/or satellite radio;
Drink holder;
Umbrella;
Book holder/eBook holder;
Timer;
Alarm Clock/Clock; and/or
Strain Gauge (measuring traction force being applied).

Further, the cervical traction device 101 can suitably be provided in a carrying case along with a set of weights 163, a set of floats, soft inserts 181, 183 to be positioned around the neck and chin and/or any of the accessories listed above.

The cervical traction device 101 illustrated in FIGS. 1-11 is just one example of a suitable cervical traction system. Another embodiment 201 is illustrated in FIGS. 12-16. In this embodiment 201, the floatation system 213 includes a pair of elongate floats 213a, 213b. A shell 217 covers the top of each float 213a, 213b. The shells 217 and/or floats 213 a, 213b are connected to one another by a cross bar 219 so the floats are spaced far enough from one another to provide a space 223 for the neck of a person to fit between the floats. The head rest 225 includes a chin rest 233 and a separate support 227 for the back of the head. The chin rest 233 and back of the head support 227 are connected to the shells of the floatation system by one or more supports (not shown). The position adjustment system 261 includes knobs 263 at each end of the shells 217. The knobs 263 can be turned to raise or lower the corresponding end of the shell 217 relative to the float 213a, 213b underneath it. For example, the knobs 263 can be attached to a threaded shaft 265 extending through the shell 217 and connected to the floats 213a, 213b such that the shell moves axially along the shaft as the knob is turned. This cervical traction device 201 can be used in a manner that is substantially similar to the cervical traction device illustrated in FIGS. 1-11.

Figure 17:
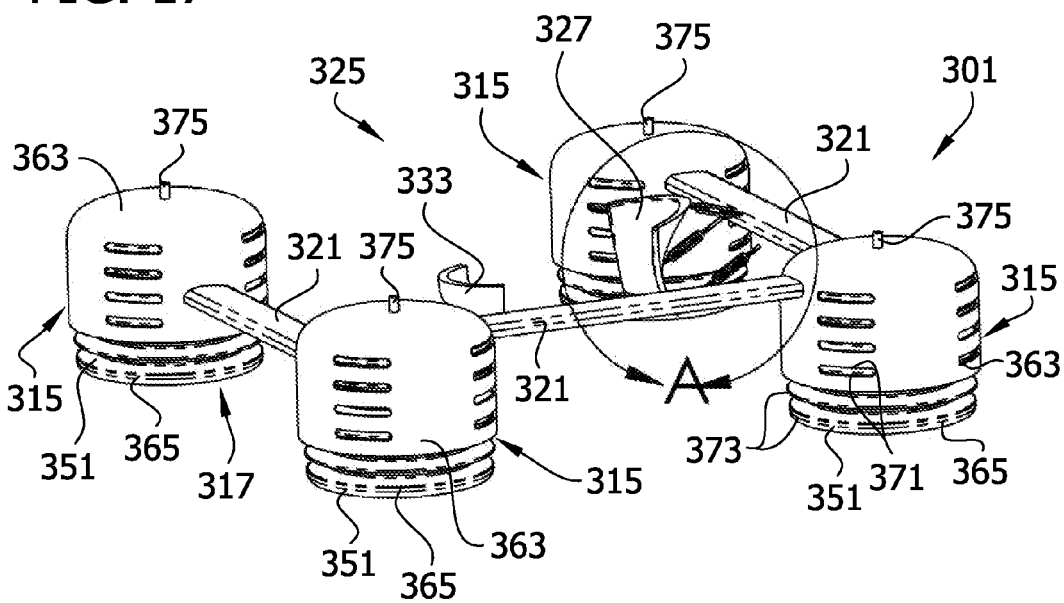
FIG. 17 is perspective of another embodiment of a cervical traction system.
Figure 18:
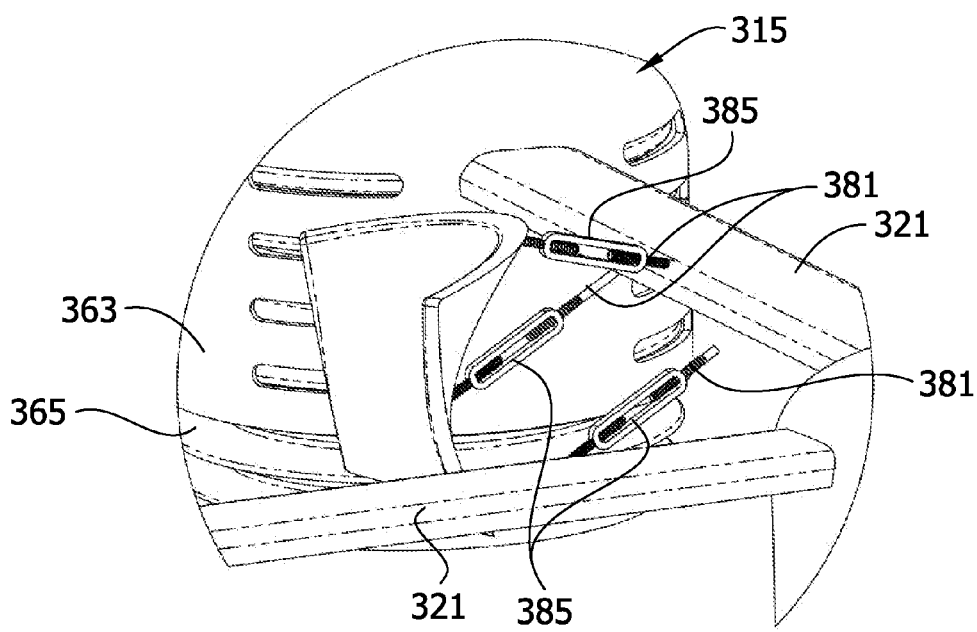
FIG. 18 is an enlarged perspective of the a portion of the cervical traction system illustrated in FIG. 17.

Another embodiment of a cervical traction device 301 is illustrated in FIGS. 17 and 18. The floatation system 313 of this device 301 includes a plurality of floats 315 connected to one another by a frame 317. The frame 317 is suitably formed by cross bars 321 extending between adjacent floats 315 and connecting them to one another. In the illustrated embodiment, there are four floats 315, but the number of floats can vary within the scope of the invention. The floats 315 are positioned at different radial positions relative to a head rest 325 supported by the floatation system. Each of the floats 315 includes a volume adjustment system 351 adapted to allow the volume of the float to be adjusted independently from the volume of the other floats. As illustrated, for example, each float 315 includes an upper portion 363 and lower portion 365. The upper and lower portions 363, 365 are arranged for telescoping movement relative to one another to increase or decrease the volume of the float 315. The sides of the upper and lower portions 363, 365 include detents 371 and ridges 373 for releasably holding the upper and lower portions at various predetermined positions (e.g., indexed positions). Each float 315 includes a valved port 375 for adding or removing air from the float. For instance, a Schrader valve 375 similar to those used to add air to tires can positioned on the top of each float 315, as illustrated.

The system 301 also includes a chin rest 333 and a separate support 327 for the back of the head. The chin rest 333 and head support 327 are suitably connected to the cross bars 321 of the frame 317 by a set of adjustable length support members 381. As illustrated, for example, the chin rest 333 and head support 327 are each connected to one of the cross bars 321 by a set of three independently adjustable turnbuckles 385.

The volume of the floats 315 can be increased or decreased to increase or decrease the amount of traction applied by the device 301. Further, the volume one or more of the floats 315 can be increased or decreased to change the orientation of the head rest 325 relative to the upper surface of the liquid to apply differential traction to the person. The turnbuckles 385 also allow the position and orientation of the head rest 325, including the chin rest 333 and the back of the head support 327, to be adjusted relative to the floatation system. The turnbuckles 385 also allow adjustment to the position of the chin rest 333 independently of the position of the back of the head support 327. One advantage is that this allows the head rest 325 to be adapted to fit various different individuals. Another advantage is the turnbuckles 385 provide another way to apply differential traction to the person.

Figure 19:
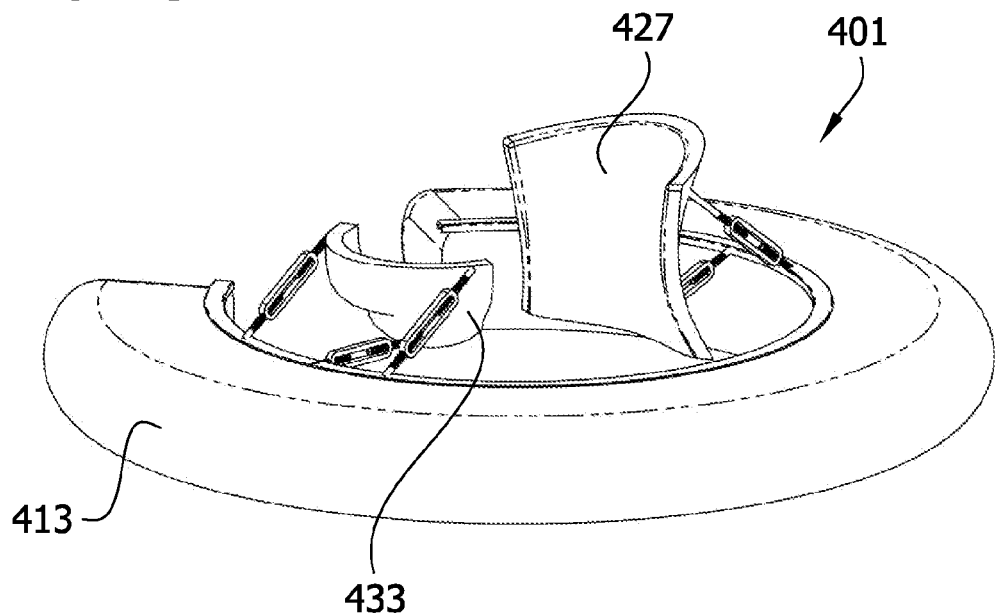
FIG. 19 is a perspective of another embodiment of a cervical traction system.
Figure 20:
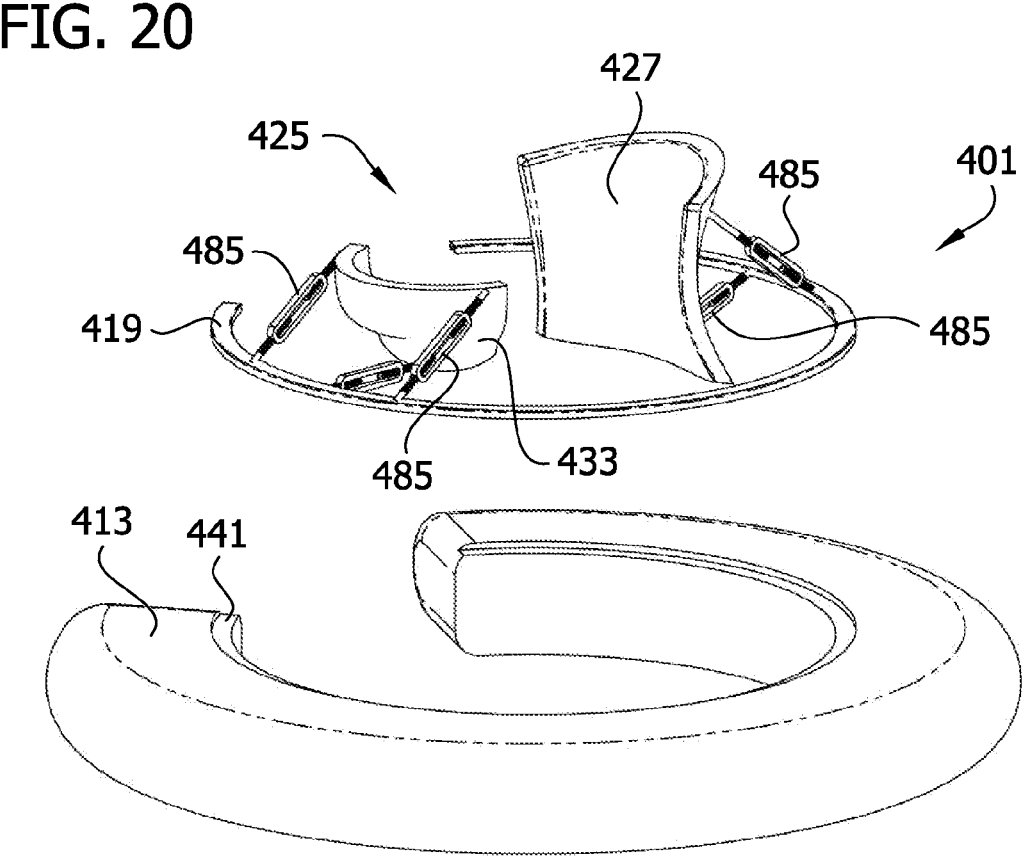
FIG. 20 is a perspective of the cervical traction system illustrated in FIG. 19 illustrating a head rest of the system in a state in which it is detached from the floatation system.

Another example of a cervical traction device 401 is illustrated in FIGS. 19 and 20. The floatation system 413 of this device is an annular float having an opening 417 in one side for entry of the person into the device. The head rest 425 includes a chin rest 433 and separate support 427 for the back of the head. The pieces 427, 433 of the two-piece head rest 425 (i.e., the chin rest and support for the back of the head) are connected to a resilient ring support 419 by turnbuckles 485, as described above. The ring support 419 is adapted to be releasably connected to the floatation system 413. For example, the ring support 419 is suitably configured to snap into a groove 441 extending around the top of the floatation system 413 at the inner margin of the float 413. The connection between the ring support 419 and floatation system 413 is strong enough so the ring support remains connected to the floatation system under normal conditions. However, the force required to separate the ring support 419 from the floatation system is low enough to result in the head rest 425 becoming detached from the floatation system 413 if a person were to accidentally fall into a pool from the side while wearing the device. This helps limit the possibility of neck injury if a person falls into the liquid while wearing the device.

Figure 21:
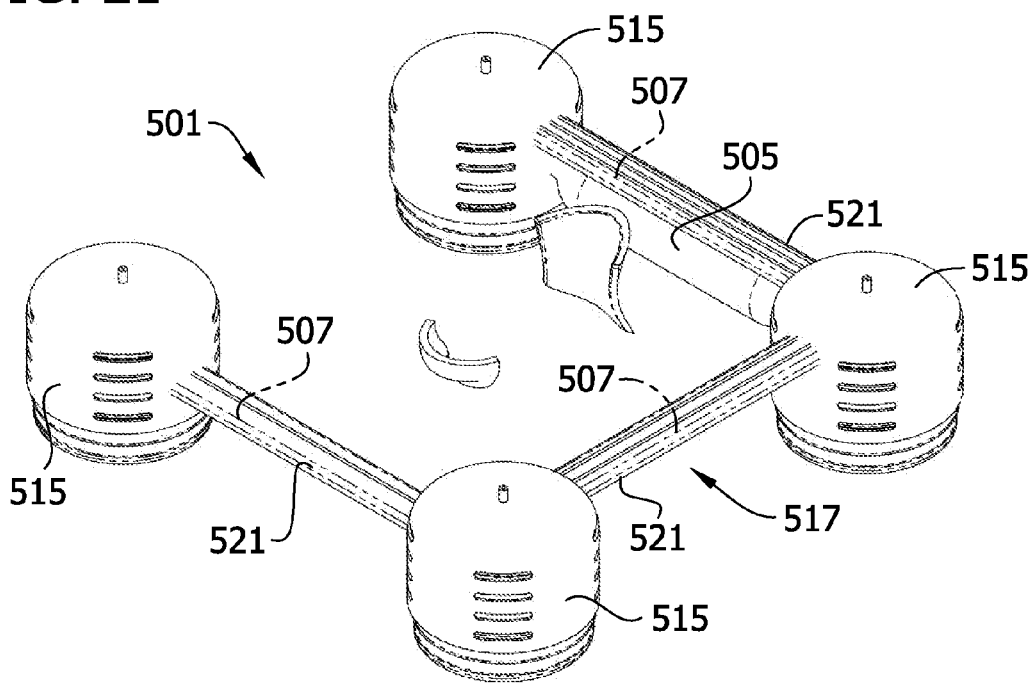
FIG. 21 is a perspective of another embodiment of a cervical traction system.
Figure 22:
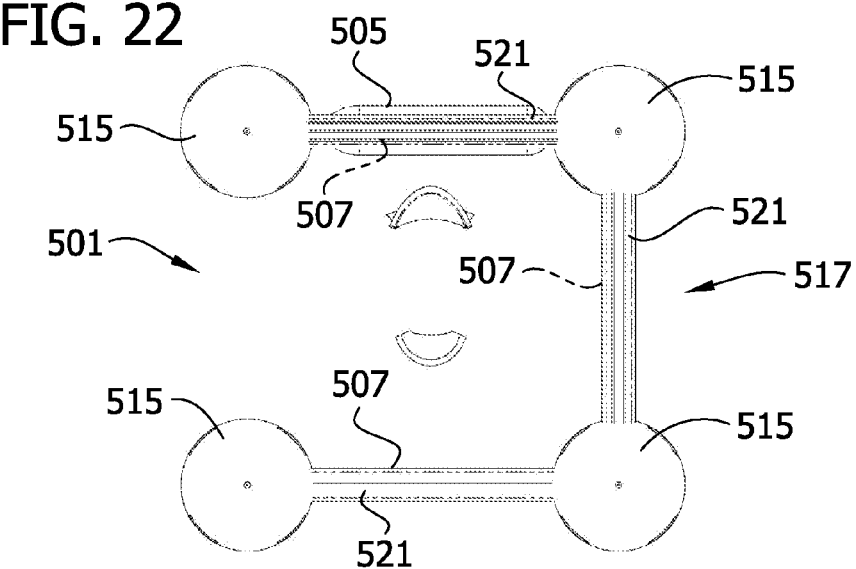
FIG. 22 is a top plan view of the cervical traction system illustrated in FIG. 21.
Figure 23:
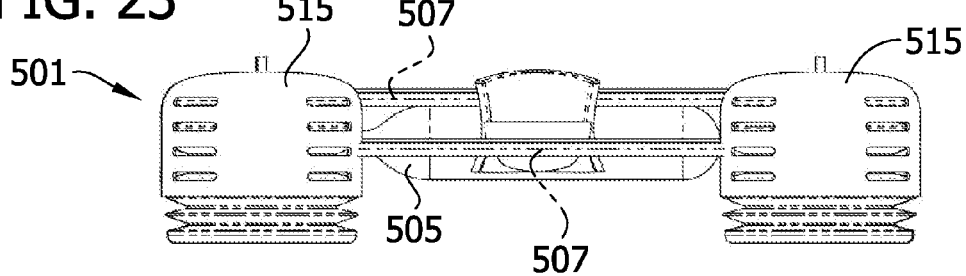
FIG. 23 is a front elevation of the cervical traction system illustrated in FIG. 20.
Figure 24:
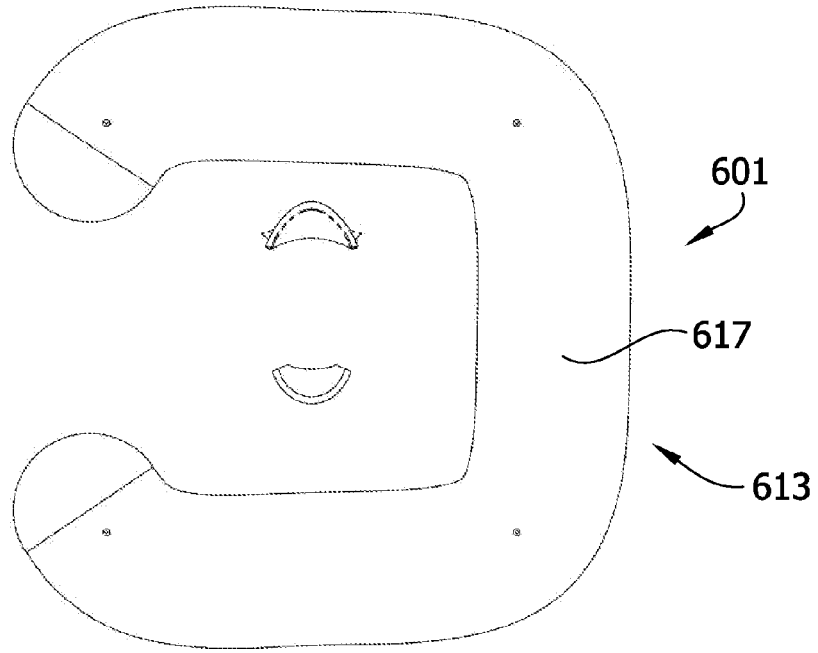
FIG. 24 is a top plan view of another embodiment of a cervical traction system.
Figure 25:
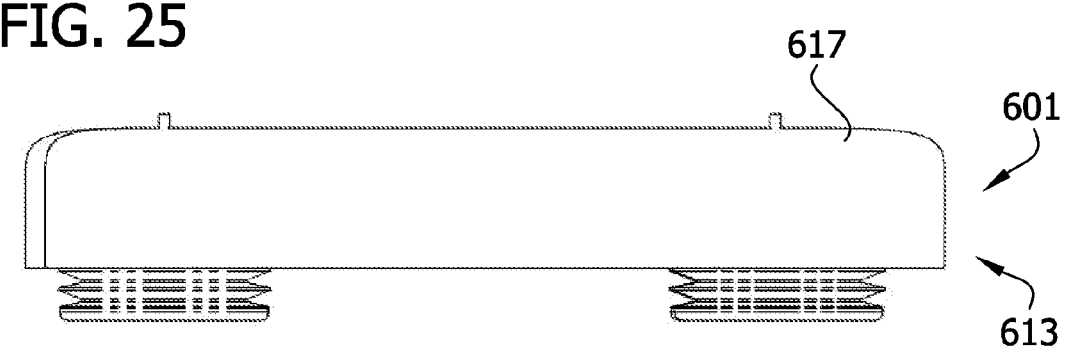
FIG. 25 is a front elevation of the cervical traction system illustrated in FIG. 24.
Figure 26:
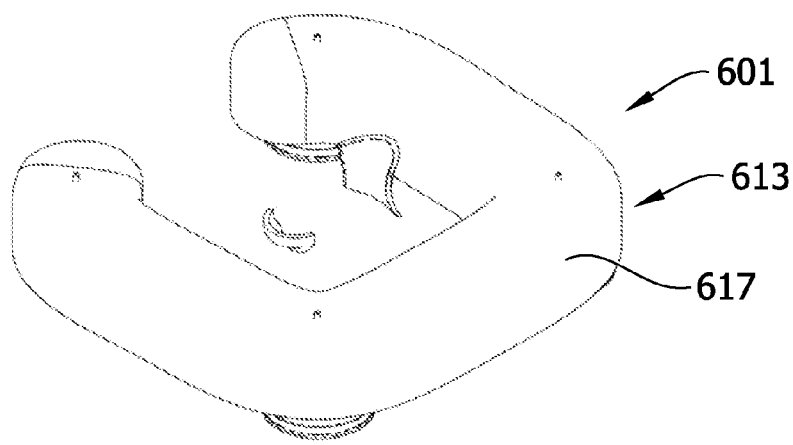
FIG. 26 is a perspective of the cervical traction system illustrated in FIG. 24.
Figure 27:
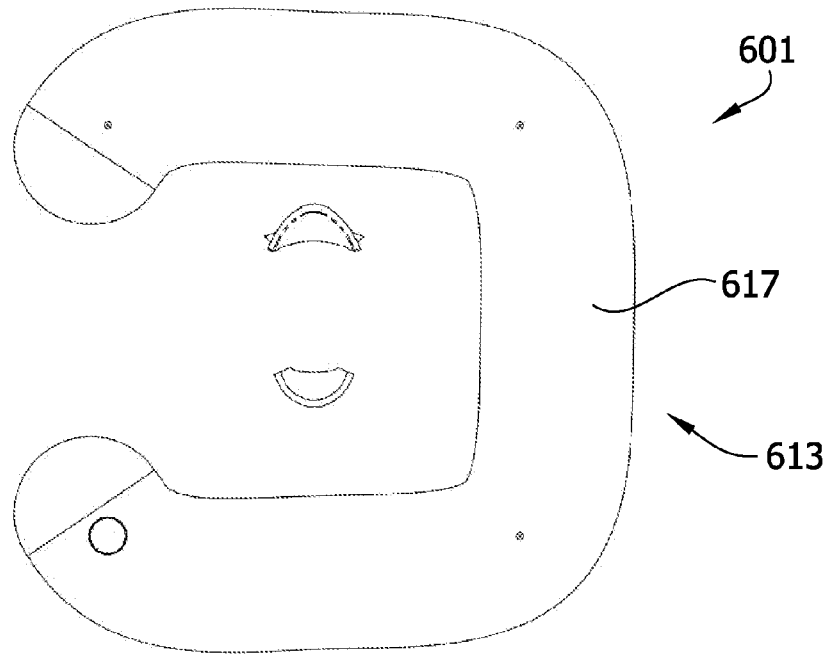
FIG. 27 is a top plan view of the cervical traction system illustrated in FIG. 24 in combination with a portable hand pump.
Figure 28:
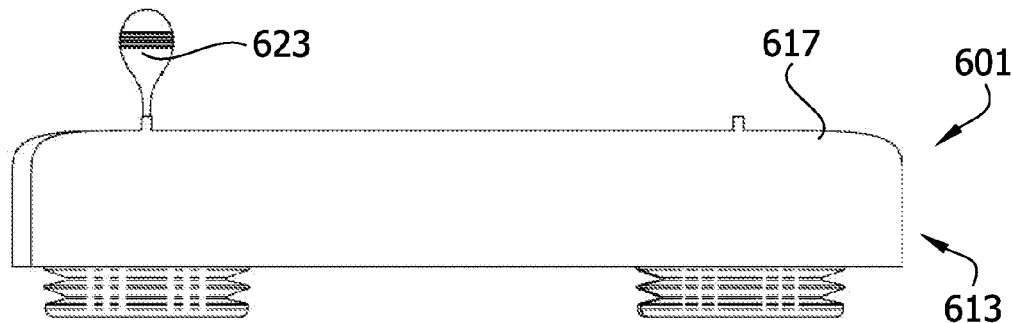
FIG. 28 is a front elevation of the cervical traction system and hand pump illustrated in FIG. 27.
Figure 29:
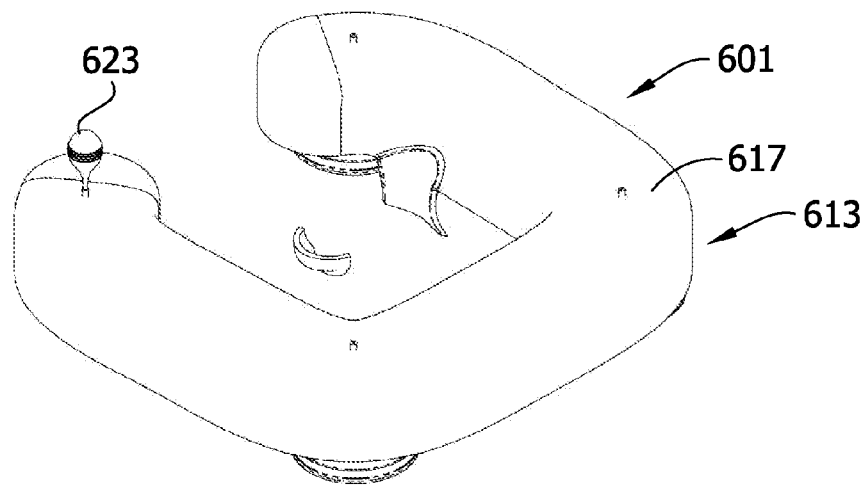
FIG. 29 is a perspective of the cervical traction system and hand pump illustrated in FIG. 27.
Figure 30:
FIG. 30 is a front elevation of the cervical traction system and hand pump illustrated in FIG. 27.

Another example of a cervical traction device 501 is illustrated in FIGS. 21-23. This device 501 is substantially similar to the device 301 illustrated in FIGS. 17-18. One difference is that this device 501 includes a built-in hand pump 505. The frame 517 also includes airways 507 extending through or along the cross bars 521 so the floats 515 are in fluid communication with one another. This equalizes pressure in the floats 515 so the hand pump 505 can be used to air up each of the floats at the same time.

Another example of a suitable cervical traction device 601 is illustrated in FIGS. 24-30. This device 601 is similar to the device 301 illustrated in FIGS. 17-18. One difference is that the floatation system 613 of this device 601 includes an upper shell 617 extending continuously over all the floats 615. FIGS. 27-30 also illustrate one embodiment of a portable hand pump 623 that may be included with the cervical traction device 601 for airing up the floats 615.

Figure 31:
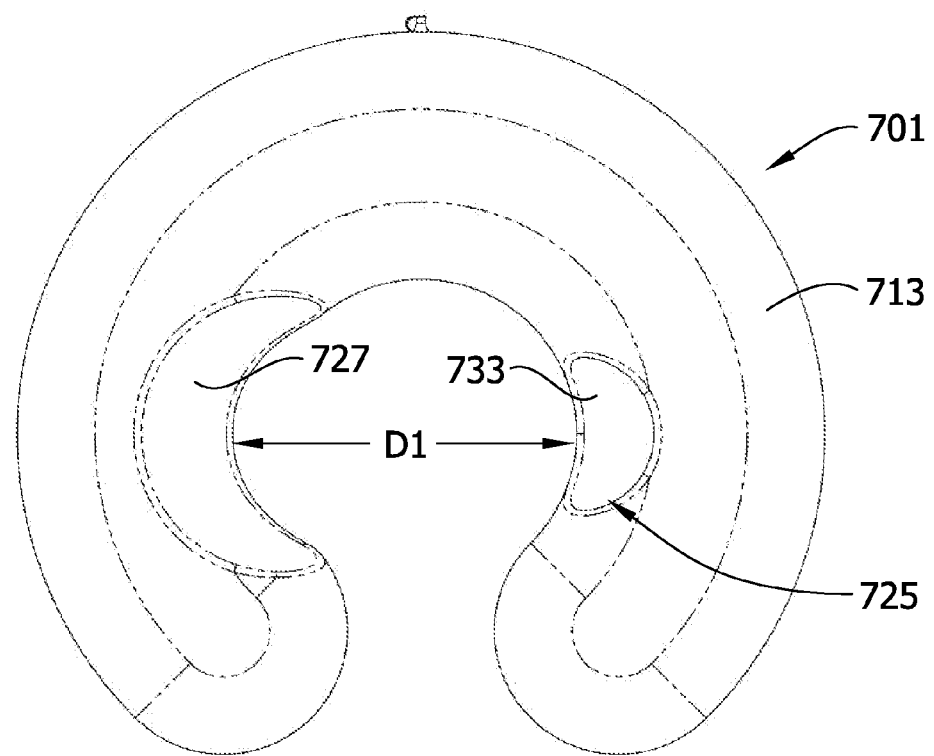
FIG. 31 is a top plan of another embodiment of a cervical traction system.
Figure 32:
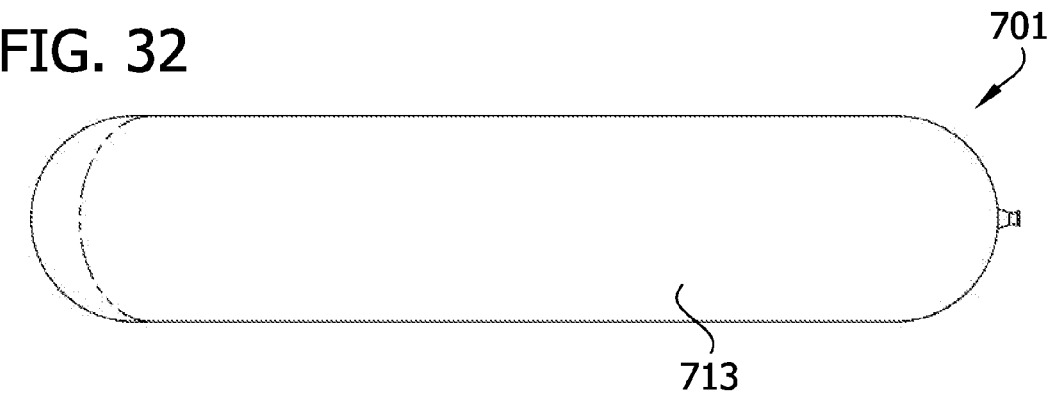
FIG. 32 is a side elevation of the cervical traction system illustrated in FIG. 31.
Figure 33:
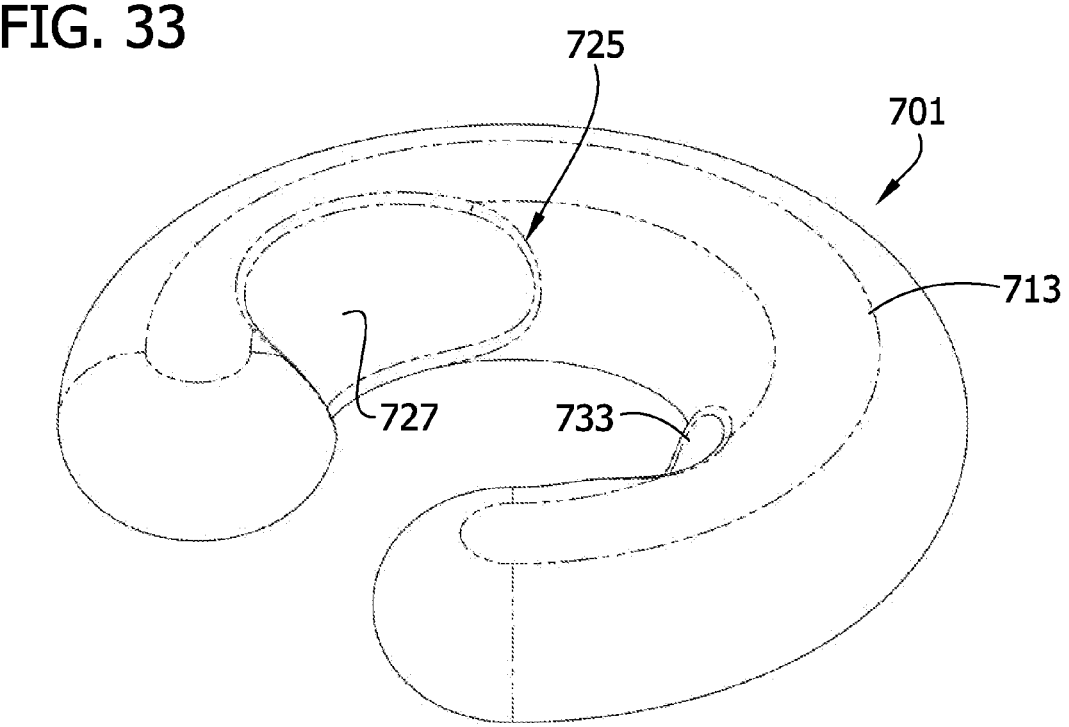
FIG. 33 is a perspective of the cervical traction system illustrated in FIG. 31.
Figure 34:
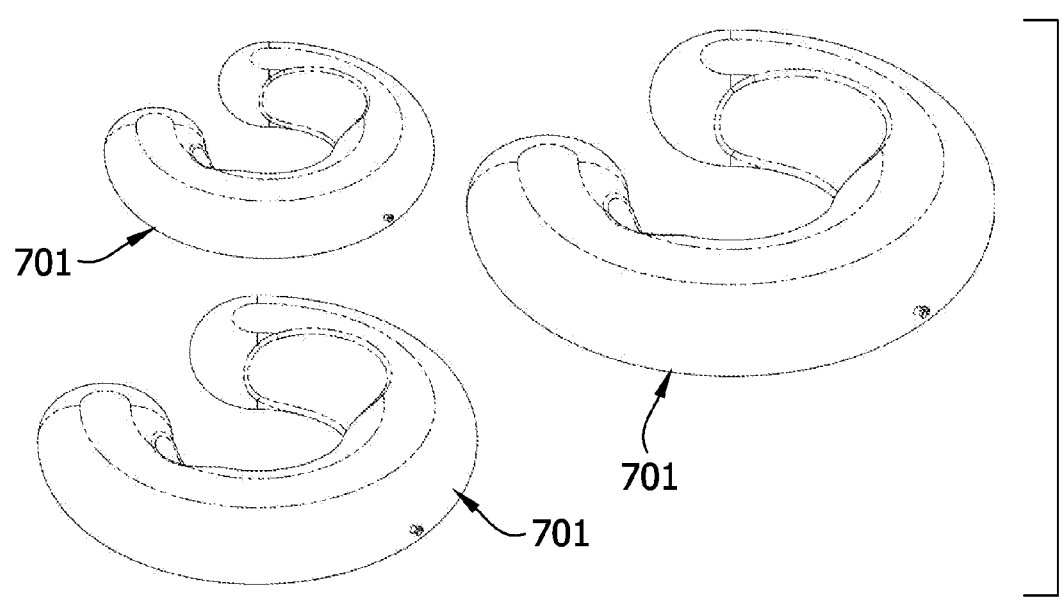
FIG. 34 is a perspective of a set of three cervical traction systems of the type illustrated in FIG. 31 that are substantially identical to one another except for they are different in size; and Corresponding reference characters indicate corresponding parts throughout the drawings.

FIGS. 31-33 illustrate another example of a cervical traction device 701. The floatation system 713 of this device includes a C-Shaped inflatable tube. The head rest 725 includes a chin rest 733 and support 727 for the back of the head that are built into the floatation system 713. The chin rest 733 and support 727 for the back of the head are spaced from one another a distance D1 that will accommodate a person's head. The cervical traction device 701 can be made in different sizes, as illustrated in FIG. 33 so that a larger device is available for use by larger people, a medium sized device is available for use by medium sized people, and a smaller device is available for use by smaller people. This embodiment does not include any features that are adapted to facilitate adjustment to the orientation of the head rest relative to the floatation system or the upper surface of the liquid. The amount of traction that is applied to person can be adjusted by increasing or decreasing the degree of inflation of the inflatable tube.

When introducing elements of the ring binder mechanisms herein, the articles "a", "an", "the" and "said" are intended to mean that there are one or more of the elements. The terms "comprising", "including" and "having" and variations thereof are intended to be inclusive and mean that there may be additional elements other than the listed elements. Moreover, the use of "forward" and "rearward" and variations of these terms, or the use of other directional and orientation terms, is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A buoyancy-based cervical traction system for applying cervical traction to a person partially submerged in a liquid, the system comprising:
   a floatation system having positive buoyancy when in the liquid,
   a head rest supported by the floatation system and adapted to support the person's head above the neck and apply traction to the neck when the person is in the liquid; and
   a position adjustment system adapted to allow selective adjustment of a position at which the head rest will be relative to an upper surface of the liquid when the person and the cervical traction system are in the liquid, the person's head is supported by the head rest, and the cervical traction system and person are floating in the liquid at equilibrium,
   wherein the position adjustment system is adapted to adjust an orientation of the head rest relative to the upper surface of the liquid and allow selective adjustment to the buoyancy of the flotation system, and
   wherein the position adjustment system comprises a plurality of buoyancy adjusters and an attachment system for releasably attaching the buoyancy adjusters to the flotation system.

2. A buoyancy-based cervical traction system as set forth in claim 1 wherein the buoyancy adjusters comprise weights.

3. A buoyancy-based cervical traction system as set forth in claim 1 wherein the buoyancy adjusters comprise floats.

4. A buoyancy-based cervical traction system as set forth in claim 1 wherein the flotation system comprises a collar extending at least partially around an opening for receiving the person's neck and the attachment system comprises a plurality of connectors secured to the collar.

5. A buoyancy-based cervical traction system as set forth in claim 4 wherein the collar has an inner margin adjacent the opening for the person's neck and an outer margin opposite the inner margin, the connectors being secured to the collar at positions that are closer to the outer margin than the inner margin.

6. A buoyancy-based cervical traction system as set forth in claim 4 wherein the connectors comprise threaded inserts secured to the bottom of the collar.

7. A buoyancy-based cervical traction system as set forth in claim 4 wherein the connectors are secured to the collar at multiple different radial positions relative to the opening for the person's neck.

8. A buoyancy-based cervical traction system as set forth in claim 7 wherein the collar is a U-shaped collar and the connectors are arranged in a U-shaped configuration generally corresponding to the shape of the collar.

9. A buoyancy-based cervical traction system as set forth in claim 1 wherein the head rest comprises a support surface for engaging the base of the person's skull at the back of the head and a chin support for engaging the person's chin.

10. A buoyancy-base cervical traction system as set forth in claim 9 wherein the chin support is positioned lower than the support surface for engaging the base of the person's skull at the back of the head when the system is in the liquid.

11. A buoyancy-based cervical traction system as set forth in claim 9 wherein the chin support is mounted on the flotation system for sliding movement toward and away from an opening for receiving the person's neck.

12. A buoyancy-based cervical traction system as set forth in claim 1 wherein the wherein the flotation system comprises a collar extending at least partially around an opening for receiving the person's neck, the collar having recessed lower surfaces on opposite sides of the opening, the recesses being adapted for at least partially receiving the person's shoulders.

13. A buoyancy-based cervical traction system as set forth in claim 1 wherein a pitch and a yaw of the head rest are adjustable independently of one another.

14. A method of applying cervical traction to a person partially submerged in a liquid, the person having a head and a neck, the head being supported above the neck by a head rest, the head rest being supported by a floatation system in the liquid, the method comprising adjusting the head rest and floatation system to adjust the position of the head relative to the surface of the liquid when the person and the floatation system are floating in the liquid at equilibrium, wherein the adjusting comprises adjusting an orientation of the head rest relative to an upper surface of the liquid and adjusting the floatation system to apply a traction force in a direction that is skewed relative to a vertical axis of the person's body by at least one of: (i) adding a weight to the floatation system; (ii) removing a weight from the floatation system; (iii) adding a float to the floatation system; and (iv) removing a float from the floatation system.

15. A buoyancy-based cervical traction system for applying cervical traction to a person partially submerged in a liquid, the system comprising:

a floatation system having positive buoyancy when in the liquid; and a head rest supportable by the floatation system so the system exerts an upward force on the person's head when the person and the system are in the liquid and the person's head is supported by the head rest, the head rest including a chin support for supporting the person's chin, wherein the chin support and floatation system are adapted so the chin support is secured to the floatation system by the weight of the person, and wherein the chin support comprises a pair of arms and the floatation system supports tracks for the arms on an upper surface of the floatation system, the tracks comprising a plurality of upwardly-facing receptacles for receiving the arms.

16. A buoyancy-based cervical traction system as set forth in claim 15 wherein the tracks comprise a plurality of ridges.

17. A buoyancy-based cervical traction system as set forth in claim 15 wherein the chin support is adapted to yield in a manner that results in separation of the chin support from the floatation system in response to any forces in excess of a cervical traction limit.

* * * * *